United States Patent
Ishikawa et al.

(10) Patent No.: US 11,464,209 B2
(45) Date of Patent: Oct. 11, 2022

(54) WALK SUPPORT DEVICE, WALK SUPPORT METHOD, AND WALK SUPPORT PROGRAM

(71) Applicant: FUJIFILM CORPORATION, Tokyo (JP)

(72) Inventors: Shigetoshi Ishikawa, Kanagawa (JP); Yasuhisa Kaneko, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 397 days.

(21) Appl. No.: 16/785,653

(22) Filed: Feb. 10, 2020

(65) Prior Publication Data

US 2020/0275637 A1    Sep. 3, 2020

(30) Foreign Application Priority Data

Feb. 28, 2019   (JP) .............................. JP2019-036588

(51) Int. Cl.
 *G06F 3/048* (2013.01)
 *A01K 15/02* (2006.01)
 *G16H 20/30* (2018.01)

(52) U.S. Cl.
 CPC ........... *A01K 15/027* (2013.01); *G16H 20/30* (2018.01)

(58) Field of Classification Search
 CPC .............................. A01K 15/027; G16H 20/30
 See application file for complete search history.

(56) References Cited

U.S. PATENT DOCUMENTS

| 10,912,282 B2* | 2/2021 | McKee ................ A01K 11/008 |
| 2012/0166322 A1* | 6/2012 | Simon ................ G06Q 10/1095 705/32 |
| 2014/0164611 A1* | 6/2014 | Molettiere ............ A61B 5/1118 709/224 |
| 2014/0331942 A1* | 11/2014 | Sarazyn ............... A01K 29/005 119/859 |

(Continued)

FOREIGN PATENT DOCUMENTS

| JP | 2008-282073 A | 11/2008 |
| JP | 2017-527264 A | 9/2017 |

(Continued)

OTHER PUBLICATIONS

English language translation of the following: Office action dated Feb. 1, 2022 from the JPO in a Japanese patent application No. 2019-036588 corresponding to the instant patent application. This office action translation is submitted now in order to supplement the understanding of the cited references which are being disclosed in the instant Information Disclosure Statement.

*Primary Examiner* — David Phantana-angkool
(74) *Attorney, Agent, or Firm* — Solaris Intellectual Property Group, PLLC

(57) ABSTRACT

Provided are a walk support device, a walk support method, and a walk support program capable of efficiently walk a pet in a short time. A walk route deriving device includes an acquiring unit that acquires exercise information for specifying the amount of exercise necessary for a pet and a deriving unit that derives a walk route of the pet including a place where the pet is running on the basis of the exercise information.

15 Claims, 15 Drawing Sheets

(56) References Cited

U.S. PATENT DOCUMENTS

| | | | | |
|---|---|---|---|---|
| 2015/0073698 | A1* | 3/2015 | Samuel | G01C 21/3438 |
| | | | | 701/422 |
| 2017/0259119 | A1* | 9/2017 | Hoffman | G16H 20/30 |
| 2020/0163311 | A1* | 5/2020 | Kelly | A01K 29/005 |
| 2020/0275637 | A1* | 9/2020 | Ishikawa | A01K 15/027 |
| 2022/0151207 | A1* | 5/2022 | Mott | A01K 27/009 |

FOREIGN PATENT DOCUMENTS

| | | |
|---|---|---|
| JP | 2018-198553 A | 12/2018 |
| WO | 2014/050118 A1 | 8/2016 |
| WO | 2016185742 A1 | 11/2016 |

\* cited by examiner

| TARGET CALORIE CONSUMPTION (kcal) | STRENGTH | |
|---|---|---|
| 0 TO 30 | 1 | ~32 |
| 31 TO 70 | 2 | |
| 71 TO 100 | 3 | |
| 101 TO 130 | 4 | |
| 131 TO 170 | 5 | |
| 171 TO 200 | 6 | |
| 201 TO 230 | 7 | |
| 231 TO 270 | 8 | |
| 271 TO 300 | 9 | |
| 301 TO | 10 | |

FIG. 5A

| WALK TIME (MIN) | CORRECTION COEFFICIENT |
|---|---|
| 0 TO 20 | 1.5 |
| 21 TO 40 | 1.2 |
| 41 TO 60 | 1 |
| 61 TO 80 | 1 |
| 81 TO 100 | 0.9 |
| 101 TO 120 | 0.8 |
| 121 TO | 0.6 |

| DOG BREED | CORRECTION COEFFICIENT |
|---|---|
| CHIHUAHUA, POMERANIAN, YORKSHIRE TERRIER, ··· | 0.6 |
| PUG, MALTESE, MINIATURE DACHSHUND, ··· | 0.8 |
| TOY POODLE, SHIBA, BULLDOG, ··· | 1 |
| GOLDEN RETRIEVER, DALMATIAN, GREYHOUND, ··· | 1.2 |
| LABRADOR RETRIEVER, AKITA, DOBERMAN, ··· | 1.5 |

| AGE (YEARS-OLD) | CORRECTION COEFFICIENT |
|---|---|
| 0 TO 1 | 0.7 |
| 2 TO 5 | 1 |
| 6 TO 8 | 1 |
| 9 TO 10 | 0.8 |
| 11 TO | 0.5 |

| IDENTIFICATION INFORMATION | | EXERCISE INFORMATION | | | | | | | | |
|---|---|---|---|---|---|---|---|---|---|---|
| PET ID | NAME | DOG BREED | AGE | GENDER | WEIGHT (g) | CASTRATION (CONTRACEPTION) | DISEASE | WALK TIME (min) | TARGET CALORIE CONSUMPTION (kcal) | START POINT | GOAL POINT |
| 1001 | NORITAMA | SHIBA | 9 | FEMALE | 2500 | NO | NO | 60 | 200 | ***** | ##### |

36

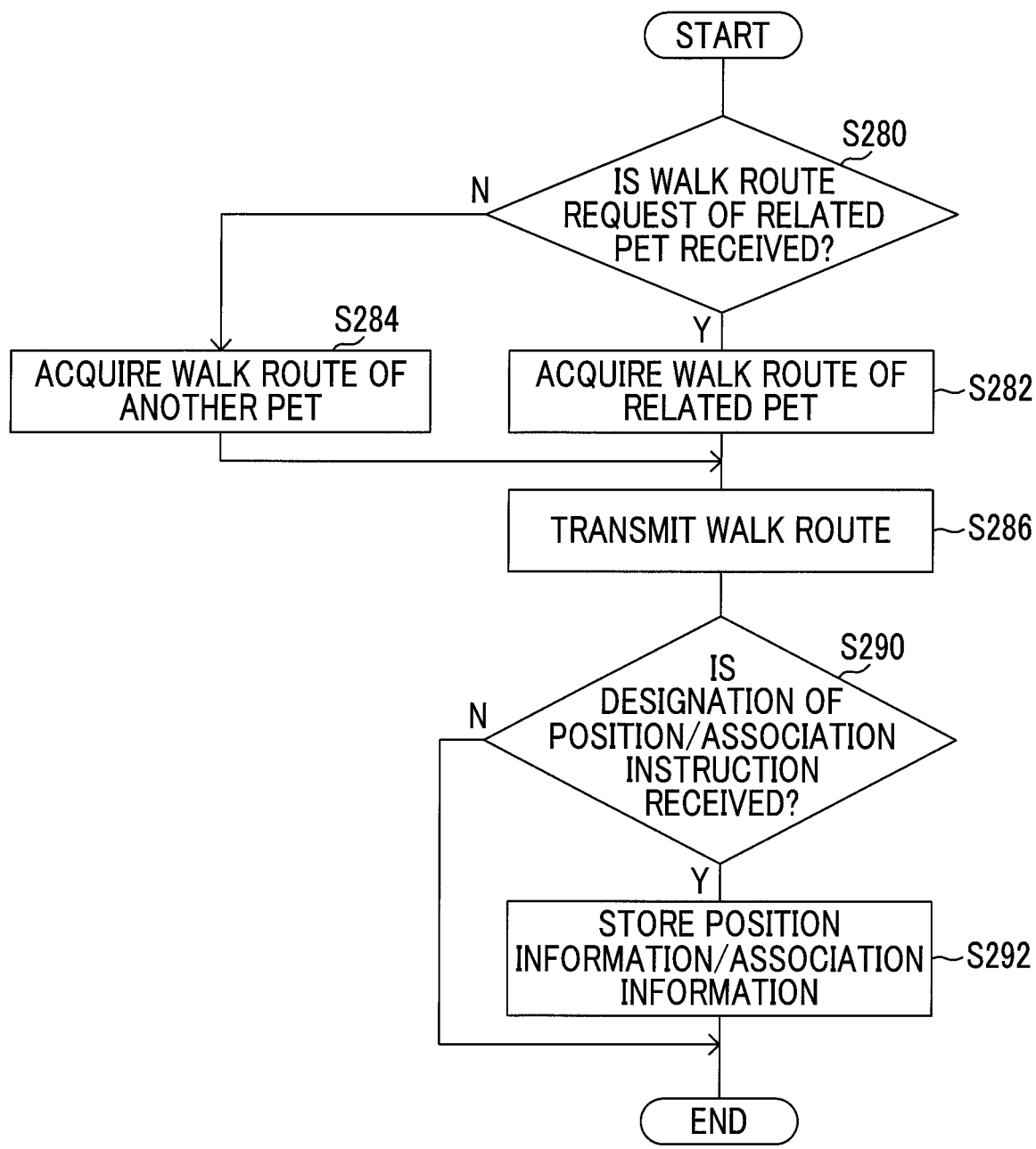

WALK SUPPORT DEVICE, WALK SUPPORT METHOD, AND WALK SUPPORT PROGRAM

CROSS-REFERENCE TO RELATED APPLICATIONS

This application is based on and claims priority under 35 USC 119 from Japanese Patent Application No. 2019-036588 filed on Feb. 28, 2019, the disclosure of which is incorporated herein by reference in its entirety.

BACKGROUND OF THE INVENTION

1. Field of the Invention

The present disclosure relates to a walk support device, a walk support method, and a computer-readable storage medium storing a walk support program.

2. Description of the Related Art

In general, walks are considered to be beneficial for improving the health of pets, and pets are walked by persons such as their owners. As a technique for supporting a pet walk, for example, JP2014-050118 discloses a technique for generating and presenting a walk route corresponding to a distance depending on the amount of activity of an animal to be walked, for example.

However, there is a case where simply taking a walk does not meet the amount of exercise necessary for pets. For example, a walk time is not determined only by the pet's dog breed, age, and the like, but is also determined by the owner's time to walk a pet, and thus, there is a case where sufficient exercise cannot be made within a predetermined walk time.

SUMMARY OF THE INVENTION

In order to solve the above problem, an object of the present disclosure is to provide a walk support device, a walk support method, and a computer-readable storage medium storing a walk support program capable of efficiently walking a pet in a short time.

In order to achieve the above object, according to a first aspect of the present disclosure, there is provided a walk support device including a processor that is configured to: acquire exercise information for specifying an amount of exercise necessary for a pet; and derive a walk route of the pet including a place where the pet is recommended to run on the basis of the exercise information.

Further, in order to achieve the above object, according to a fifteenth aspect of the present disclosure, there is provided a walk support method including: by a processor: acquiring exercise information for specifying an amount of exercise necessary for a pet; and deriving a walk route of the pet including a place where the pet is recommended to run.

In addition, in order to achieve the above object, according to a sixteenth aspect of the present disclosure, there is provided a computer-readable storage medium storing a walk support program for causing a computer to: acquire exercise information for specifying an amount of exercise necessary for a pet; and derive a walk route of the pet including a place where the pet is recommended to run on the basis of the exercise information.

BRIEF DESCRIPTION OF THE DRAWINGS

FIG. 5A is a diagram showing an example of walk time correction coefficient information according to the embodiment.

FIG. 5B is a diagram showing an example of dog breed correction coefficient information according to the embodiment.

FIG. 5C is a diagram showing an example of age correction coefficient information according to the embodiment.

FIG. 6 is a diagram showing an example of basic information according to the embodiment.

FIG. 16 is a flowchart showing an example of a walk route providing process executed by the walk route deriving device according to the embodiment.

DESCRIPTION OF THE PREFERRED EMBODIMENTS

Hereinafter, exemplary embodiments for executing the technology of the present disclosure will be described in detail with reference to the accompanying drawings.

Figure 1:
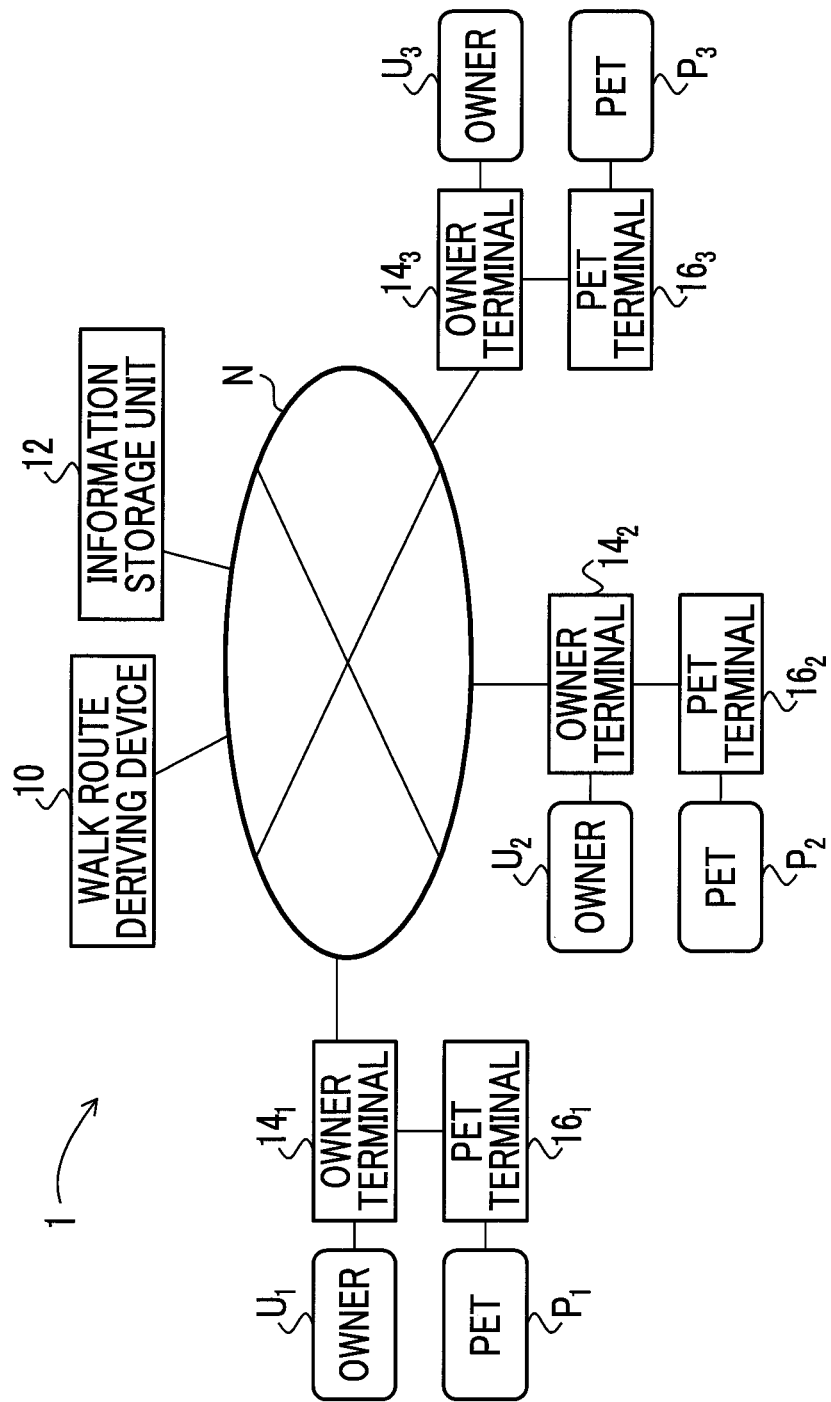
FIG. 1 is a block diagram showing an example of a configuration of a walk support system according to an embodiment.

First, a walk support system according to an embodiment of the invention will be described with reference to FIG. 1. FIG. 1 shows a block diagram showing an example of a configuration of the walk support system according to the present embodiment. As shown in FIG. 1, the walk support system 1 according to this embodiment includes a walk route deriving device 10, an information storage unit 12, a plurality of (in FIG. 3, for example, three) owner terminals 14 ($14_1$ to $14_3$), and a plurality of (in FIG. 1, for example, three) pet terminals 16 ($16_1$ to $16_3$). The walk route deriving device 10, the information storage unit 12, and each of the owner terminals 14 are connected to a network N, and is able to perform communication through the network N. This embodiment is not limiting, and at least one of the walk route deriving device 10, the information storage unit 12, or the owner terminal 14 may be configured to communicate with other devices without through the network N. Further, each of the plurality of owner terminals 14 is connected to be able to communicate with the pet terminal 16 corresponding to each of pets $P_1$ to $P_3$ of owners $U_1$ to $U_3$ who own the owner terminals 14 through communication that does not pass through the network N, for example, through wireless communication or wired communication.

In this embodiment, in a case where the owner terminals $14_1$ to $14_3$ are not distinguished from each other, the owner terminals $14_1$ to $14_3$ are collectively referred to as "owner terminals 14". Similarly, in a case where the pet terminals $16_1$ to $16_3$, the owners $U_1$ to $U_3$, and the pets $P_1$ to $P_3$ are collectively handled, the pet terminals $16_1$ to $16_3$, the owners $U_1$ to $U_3$, and the pets $P_1$ to $P_3$ are referred to as "pet terminals 16", "owners U", and "pets P". The owners U of this embodiment correspond to an example of persons who take a walk with the pets of the present disclosure.

The walk route deriving device 10 has a function of deriving walk routes suitable for the owners U to take a walk with the pets P and transmitting the derived walk routes to the owner terminals 14. Although details will be described later, a walk route of this embodiment includes a place where a pet P is recommended to run (hereinafter, referred to as a "running place"). In the walk route deriving device 10 of this embodiment, although it is recommended that the pet P should run, for simplicity of description, it is assumed that the pet P runs. For example, a "recommended running distance" is simply referred to as a "running distance".

Figure 2:
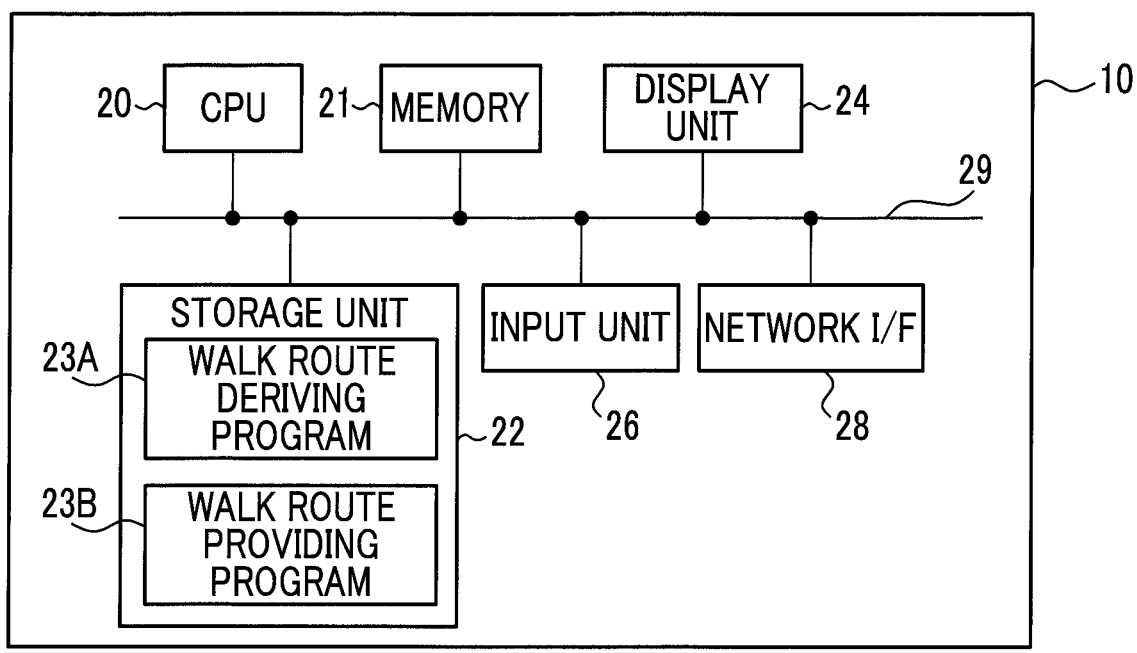
FIG. 2 is a block diagram showing an example of a hardware configuration of a walk route deriving device according to the embodiment.

Referring to FIG. 2, an example of a hardware configuration of the walk route deriving device 10 according to this embodiment will be described. As shown in FIG. 2, the walk route deriving device 10 includes a central processing unit (CPU) 20, a memory 21 that serves as a temporary storage area, and a non-volatile storage unit 22. Further, the walk route deriving device 10 includes a display unit 24 such as a liquid crystal display, an input unit 26 such as a keyboard or a mouse, and a network interface (I/F) 28 connected to the network N. The CPU 20, the memory 21, the storage unit 22, the display unit 24, the input unit 26, and the network I/F 28 may be connected to a bus 29 to be able to communicate with each other.

The storage unit 22 is realized by a hard disk drive (HDD), a solid state drive (SSD), a flash memory, and the like. In the storage unit 22 that is a storage medium, a walk route deriving program 23A and a walk route providing program 23B are stored. The CPU 20 reads out the walk route deriving program 23A and the walk route providing program 23B from the storage unit 22, respectively, develops the read-out walk route deriving program 23A and walk route providing program 23B in the memory 21, and executes the developed walk route deriving program 23A and walk route providing program 23B, respectively. The walk route deriving program 23A of this embodiment is an example of a support program of the present disclosure.

Figures 3, 4:
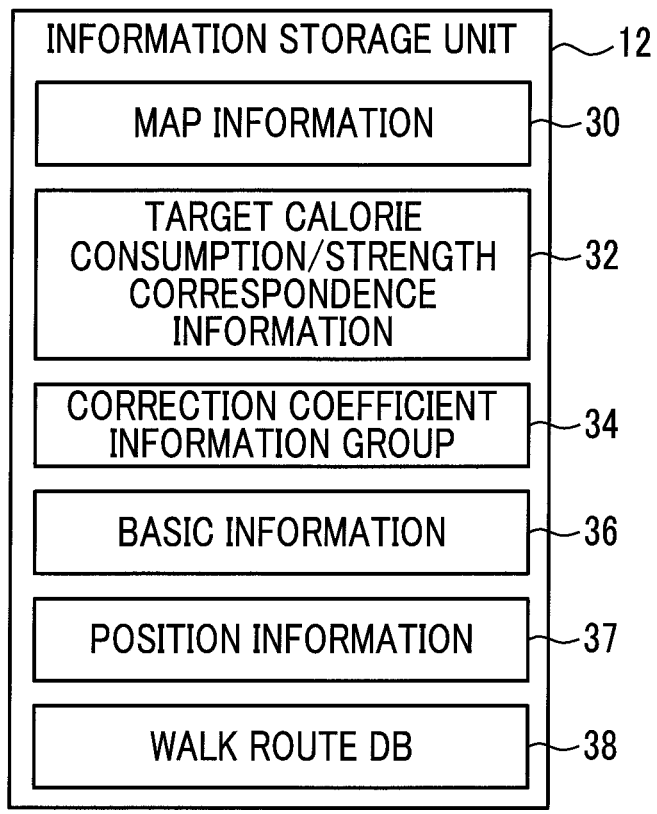
FIG. 3 is a block diagram showing an example of a configuration of an information storage unit according to the embodiment.
FIG. 4 is a diagram showing an example of target calorie consumption/strength correspondence information according to the embodiment.

Further, the information storage unit 12 of this embodiment is a cloud type external storage that is usable so-called online. As shown in FIG. 3, in the information storage unit 12, map information 30, target calorie consumption/strength correspondence information 32, a correction coefficient information group 34, basic information 36, position information 37, and a walk route database (DB) 38 are stored.

First, the map information 30 will be described. The map information 30 is information in which a general map is associated with information necessary for deriving a walk route of the pet P, such as a place where the pet can run or a place where the pet can suitably rest. The place where the pet can run is associated with a strength (details of which will be described later).

Next, the target calorie consumption/strength correspondence information 32 will be described. FIG. 4 shows an example of the target calorie consumption/strength correspondence information 32. The target calorie consumption/strength correspondence information 32 is information that represents a correspondence relationship between target calorie consumption of the pet P and the strength. Here, the "strength" is an index that represents a level at which the pet P runs on a walk, in which as a numerical value indicating the strength becomes larger, a running level becomes stronger, that is, the level of exercise becomes higher compared with a case where the pet walks. Accordingly, as the numerical value indicating the strength becomes larger, at least one of a running distance or a running time becomes longer. In this embodiment, as the value of the strength becomes larger, the running distance that becomes longer is associated in advance, and its correspondence relationship (not shown) is stored in the information storage unit 12. Further, there is a case where, as the numerical value indicating the strength becomes larger, the load caused by running becomes severer and the amount of exercise becomes larger. For example, as the numerical value indicating the strength becomes larger, the speed becomes faster.

In the example of the target calorie consumption/strength correspondence information 32, as the target calorie consumption becomes larger, the associated strength value becomes larger.

Next, the correction coefficient information group 34 will be described. In the walk route deriving device 10 of this embodiment, a running distance or the like is determined on the basis of a value obtained by correcting the strength using a correction coefficient determined in accordance with each piece of exercise information for specifying a walk time and the amount of exercise necessary for the pet P, in this example, for example, on the basis of a value obtained by multiplying the strength by the correction coefficient. The correction coefficient information group 34 includes a plurality of pieces of correspondence relationship information indicating a correspondence relationship between each piece of exercise information for specifying the walk time and the amount of exercise necessary for the pet P, and the correction coefficient.

FIG. 5A shows an example of walk time correction coefficient information 34A indicating a correspondence relationship between a walk time and a correction coefficient. In the example of the walk time correction coefficient information 34A, as the walk time becomes shorter, a value of its associated correction coefficient becomes larger. In other words, as the walk time becomes shorter, the strength value becomes larger, and the amount of exercise of the pet P becomes larger.

Further, FIG. 5B shows an example of dog breed correction coefficient information 34B indicating a correspondence relationship between a dog breed and a correction coefficient. The amount of exercise necessary for each dog breed of the pet P varies. Accordingly, in the walk route deriving device 10 of this embodiment, in accordance with the dog breed of the pet P, specifically, in accordance with the breed of a dog since dogs are targeted as the pets P in the walk route deriving device 10 of this embodiment, correction coefficients are predetermined. In the example of the dog breed correction coefficient information 34B, as the amount of exercise necessary in accordance with the dog breed becomes larger, a value of its associated correction coefficient becomes larger. Accordingly, as the amount of exercise necessary in accordance with the dog breed becomes larger, the strength value becomes larger, and the amount of exercise of the pet P becomes larger.

Further, FIG. 5C shows an example of age correction coefficient information 34C indicating a correspondence relationship between an age and a correction coefficient. The amount of exercise necessary varies in accordance with the age of the pet P. Accordingly, in the walk route deriving device 10 of this embodiment, the correction coefficient is determined in advance in accordance with the age of the pet P. In the example of the age correction coefficient information 34C, as the age of the pet P becomes larger, a value of its associated correction coefficient becomes larger. Accordingly, as the amount of exercise necessary in accordance with the age becomes larger, the strength value becomes larger, and the amount of exercise of the pet P becomes larger.

In addition, as an example of information relating to the correction coefficient included in the correction coefficient information group 34, information indicating a correspondence relationship between a gender and a correction coefficient may be used. In this embodiment, as an example, in the information indicating the correspondence relationship between the gender and the correction coefficient, since a necessary amount of exercise in a case where the gender of the pet P is male is larger than that in a case where the gender of the pet P is female, a large correction coefficient is associated. Accordingly, the strength value in a case where the gender of the pet P is male is larger than that in a case where the gender of the pet P is female.

Further, as another example, information indicating a correspondence relationship between a weight and a correction coefficient may be used. In this embodiment, as an example, in the information indicating the correspondence relationship between the weight and the correction coefficient, as the weight of the pet P becomes larger, the necessary amount of exercise becomes larger, and thus, a larger correction coefficient is associated. An appropriate weight varies in accordance with a dog breed, an age, a gender, and the like. Accordingly, from the viewpoint of diet of the pet P, as the information indicating the correspondence relationship between the weight and the correction coefficient, as a difference between an appropriate weight and a current weight of the pet P becomes larger, it is preferable that information in which a larger correction coefficient is associated is used. Further, in a case where the weight of the pet P excessively exceeds the appropriate weight, there is a case where it is not preferable to perform intense exercise. For this reason, in a case where the weight exceeds a certain threshold value, it is preferable that as the weight becomes larger, its associated correction coefficient value becomes smaller.

Further, as another example, information indicating a correspondence relationship between the presence/absence of castration (contraception) and a correction coefficient may be used. Generally, in a case where castration (contraception) is performed, the pet P tends to become fat. Accordingly, in this embodiment, as an example, in the information indicating the correspondence relationship between the presence or absence of castration (contraception) and the correction coefficient, in a case where the pet P is castrated (is subjected to contraception), the correction coefficient for increasing the strength value is associated.

Further, as another example, information indicating a correspondence relationship between the presence or absence of disease in the pet P and a correction coefficient may be used. Generally, it is not preferable to perform intense exercise in a case where the pet has disease. Further, as the degree (progression) of disease becomes severe, it is not preferable to perform intense exercise. Accordingly, in this embodiment, as an example, in the information indicating the correspondence relationship between the presence or absence of disease and the correction coefficient, in a case where the pet P has disease, the correction coefficient for decreasing the strength value is associated. In accordance with the type of disease or the above-described degree of disease, the correction coefficient may be associated. Further, for example, in a case where the pet P has disease, the correction coefficient for excluding the running place from the walk route of the pet P may be associated. In this embodiment, in a case where the correction coefficient is set to "0", the strength value becomes "0", and the running place is not included in the walk route derived by the walk route deriving device 10.

Next, the basic information 36 will be described. FIG. 6 shows an example of the basic information 36. As shown in FIG. 6, the basic information 36 of this embodiment includes identification information, exercise information, and each piece of information on a walk time, target calorie consumption, a start point, and a goal point. The identification information is information for identifying the pet P, and in this embodiment, a "pet identifier (ID)" of the pet P, and a "name" of the pet P are used as the identification information. The identification information is not limited to this embodiment, and information relating to an owner U of the pet P may be used as the identification information.

On the other hand, the exercise information is information for specifying the amount of exercise necessary for the pet P. In this embodiment, as an example of the exercise information, information relating to a "dog breed", an "age", a "gender", a "weight", "castration (contraception)", and "disease" is used. As described above, in accordance with the exercise information, the amount of exercise necessary for the pet P varies. In the walk support system 1 of this embodiment, information (parameters) that affects the amount of exercise necessary for the pet P is referred to as "exercise information", but specific information is not limited this embodiment. For example, as the exercise information, the body fat percentage or obesity level of the pet P may be used.

Further, the walk time is a time necessary for the owner U to walk the pet P. As will be described later, in the walk support system 1 of this embodiment, the owner U may set the walk time. In a case where there is no designation from the owner U, in an initial setting in the basic information 36, the walk time is set to 60 minutes. The walk time is not limited to this embodiment, and at least one of a time point when a walk is started or a time point when the walk is ended may be included in the basic information 36.

Further, the target calorie consumption is calorie targeted for consumption by the pet P by taking a walk. As will be described later, in the walk support system 1 of this embodiment, the owner U may set the target calorie consumption. For example, the walk route deriving device 10 may derive the target calorie consumption from the dog breed, the age, the gender, the amount of meal, and the like of the pet P. In a case where the pet P is a dog, the amount of necessary energy is obtained from a resting energy requirement (RER)

expressed by the following equation (1). Further, a daily energy requirement (DER) of the pet P is obtained by the following equation (2). The "activity coefficient" in the equation (2) is a multiple according to a life stage of the pet P.

$$RER = 70 \times weight^{0.75} \quad (1)$$

$$DER = RER \times activity\ coefficient \quad (2)$$

Further, the start point is position information of a point where the pet P starts a walk, and the goal point is position information of a point where the pet P ends the walk. As will be described later, in the walk support system 1 of this embodiment, the owner 1 may set the start point and the goal point. In a case where there is no designation from the owner U, in the initial setting in the basic information 36, both of the start point and the goal point are set to positions of the owner terminal 14 in a case where start of the walk route deriving process in the owner terminal 14 is executed (which will be described later).

Next, the position information 37 will be described. The position information 37 is information relating to a position of another pet P with respect to a specific pet P. As the position information 37, for example, a position (address) where the other pet P lives, a walk route of the other pet P, a position of a resting place in the walk route of the other pet P, or the like may be used. As will be described later, in the walk support system 1 of this embodiment, the owner U may set the correction coefficient information group 34.

Next, the walk route DB 38 will be described. The walk route DB 38 is a database in which a plurality of pieces of information indicating walk routes derived by the walk route deriving device 10 are stored. As an example, in this embodiment, for each pet P, a pet ID of the pet P and information indicating a derived walk route are stored in the walk route DB 38 in association with each other. Further, in the walk route DB 38 of this embodiment, identification information of other pets P relating to the pet P for which the walk route is derived, or identification information of other owners U or pets P of the other owners U relating to the owner U of the pet P for which the walk route is derived is associated.

On the other hand, as the owner terminal 14, for example, a smartphone, a tablet computer, and the like may be used. In this embodiment, a configuration in which the owner terminal 14 is formed as one device has been described, but a configuration in which the owner terminal 14 may be formed as a plurality of devices may be used.

Figure 7:
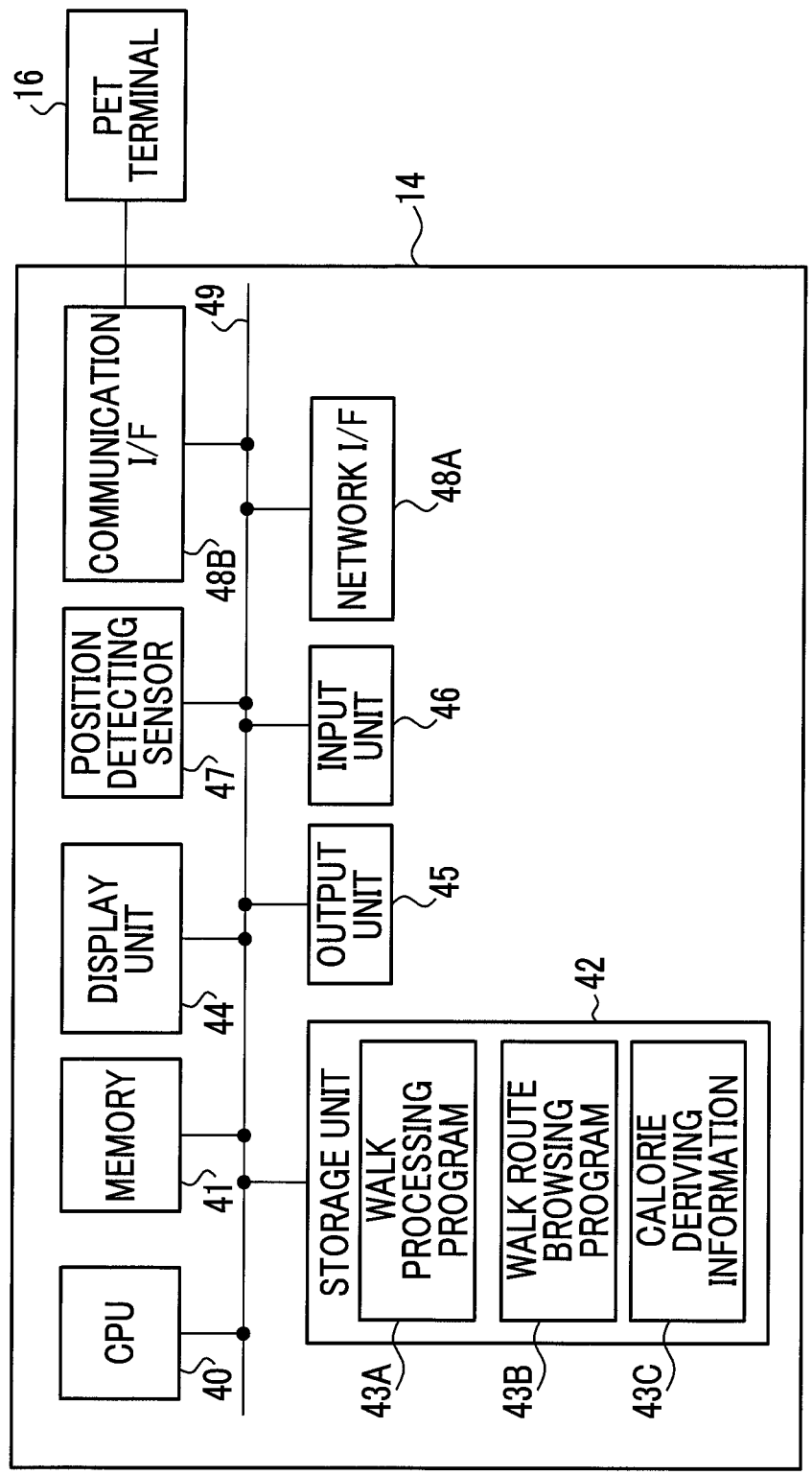
FIG. 7 is a block diagram showing an example of a hardware configuration of an owner terminal according to the embodiment.

With reference to FIG. 7, an example of a hardware configuration of the owner terminal 14 of this embodiment will be described. As shown in FIG. 7, the owner terminal 14 includes a CPU 40, a memory 41 that is a temporary storage area, and a non-volatile storage unit 42. Further, the owner terminal 14 includes a display unit 44 such as a liquid crystal display, an output unit 45 such as a speaker, an input unit 46 such as a keyboard, a position detecting sensor 47 such as a global positioning system (GPS), a network I/F 48A connected to the network N, and a communication I/F 48B for performing communication with the pet terminal 16. The CPU 40, the memory 41, the storage unit 42, the display unit 44, the output unit 45, the input unit 46, the position detecting sensor 47, the network I/F 48A, and the communication I/F 48B are connected to the bus 49 to be able to communicate with each other. As an example, the owner terminal 14 of this embodiment includes a touch panel display having functions of the display unit 44 and the input unit 46.

The storage unit 42 is realized by an HDD, an SSD, a flash memory, and the like. The storage unit 42 that is a storage medium stores a walk processing program 43A, a walk route browsing program 43B, and calorie deriving information 43C. The CPU 40 reads out the walk processing program 43A and the walk route browsing program 43B from the storage unit 42, respectively, develops the read-out walk processing program 43A and walk route browsing program 43B in the memory 41, and executes the developed walk processing program 43A and walk route browsing program 43B, respectively.

On the other hand, the pet terminal 16 of this embodiment is a wearable device carried by the pet P. For example, the pet terminal 16 of this embodiment measures the number of steps in a walk of the pet P, derives a movement distance based on the number of steps, and transmits information indicating the derived movement distance to the owner terminal 14.

Figure 8:
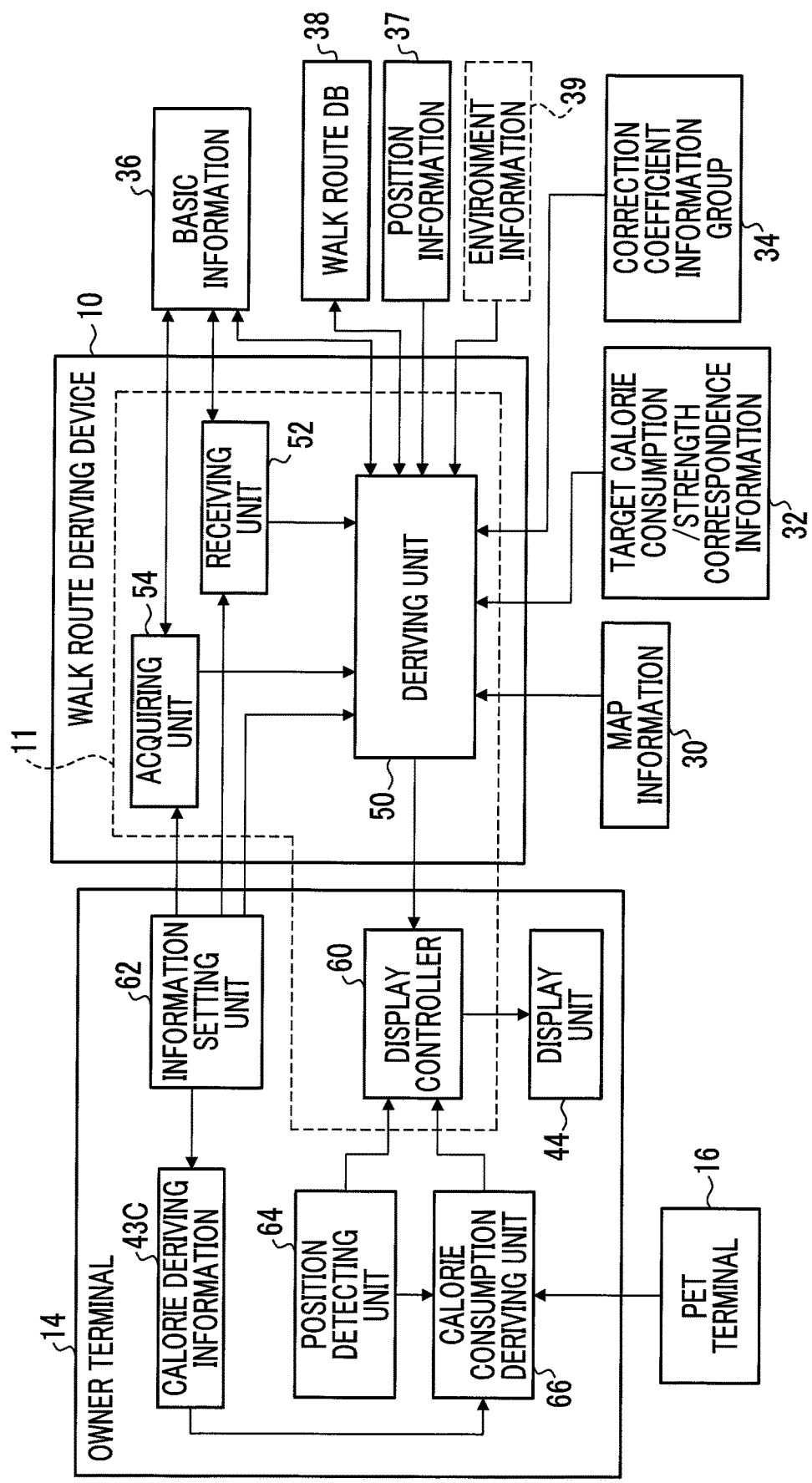
FIG. 8 is a functional block diagram showing an example of a configuration of the walk route deriving device and the owner terminal according to the embodiment.

Next, with reference to FIG. 8, functional configurations of the walk route deriving device 10 and the owner terminal 14 of this embodiment will be described. FIG. 8 shows a functional block diagram showing an example of configurations of the walk route deriving device 10 and the owner terminal 14 of this embodiment.

As shown in FIG. 8, the walk route deriving device 10 includes a deriving unit 50, a receiving unit 52, and an acquiring unit 54. The CPU 20 of the walk route deriving device 10 functions as the deriving unit 50, the receiving unit 52, and the acquiring unit 54 as the CPU 20 executes the walk route deriving program 23A. Further, the owner terminal 14 includes a display controller 60, an information setting unit 62, a position detecting unit 64, and a calorie consumption deriving unit 66. The CPU 40 of the owner terminal 14 functions as the display controller 60, the information setting unit 62, the position detecting unit 64, and the calorie consumption deriving unit 66 as the CPU 40 executes the walk processing program 43A. The deriving unit 50, the receiving unit 52, the acquiring unit 54, and the display controller 60 of this embodiment form the walk support device 11.

The acquiring unit 54 of the walk route deriving device 10 acquires the basic information 36 or the like from the information setting unit 62 of the owner terminal 14. The acquiring unit 54 stores the acquired basic information 36 in the information storage unit 12 as the basic information 36, and outputs the result to the deriving unit 50. The receiving unit 52 receives designation of a walk time designated by the information setting unit 62 of the owner terminal 14. The receiving unit 52 stores the received walk time in the information storage unit 12 as the basic information 36, and outputs the result to the receiving unit 52. The deriving unit 50 derives the walk route of the pet P on the basis of each of the map information 30, the target calorie consumption/strength correspondence information 32, the correction coefficient information group 34, the basic information 36, the position information 37, the walk route DB 38, and environment information 39, and transmits the derived walk route to the owner terminal 14.

On the other hand, the information setting unit 62 has a function of causing the owner U to set the basic information 36. The basic information 36 set by the owner U is transmitted to the owner terminal 14. Further, information necessary for consumption of calorie of the pet P among the basic information 36 is stored in the storage unit 22 as the calorie deriving information 43C. As an example, in this embodiment, the weight of the pet P is used as the calorie deriving information 43C.

Further, the position detecting unit 64 has a function of detecting the position of the owner terminal 14 by the position detecting sensor 47, and outputs the detection result to the calorie consumption deriving unit 66 and the display controller 60. The calorie consumption deriving unit 66 has a function of deriving calorie consumption consumed by the pet P and the owner U by a walk on the basis of the calorie deriving information 43C, the detection result of the position detecting unit 64, and information indicating the amount of movement of the pet obtained from the pet terminal 16. Further, the display controller 60 controls the display unit 44 to display the walk route of the pet P derived by the deriving unit 50, a current position of the pet P (owner U), and calorie consumption in a walk.

Figure 9:
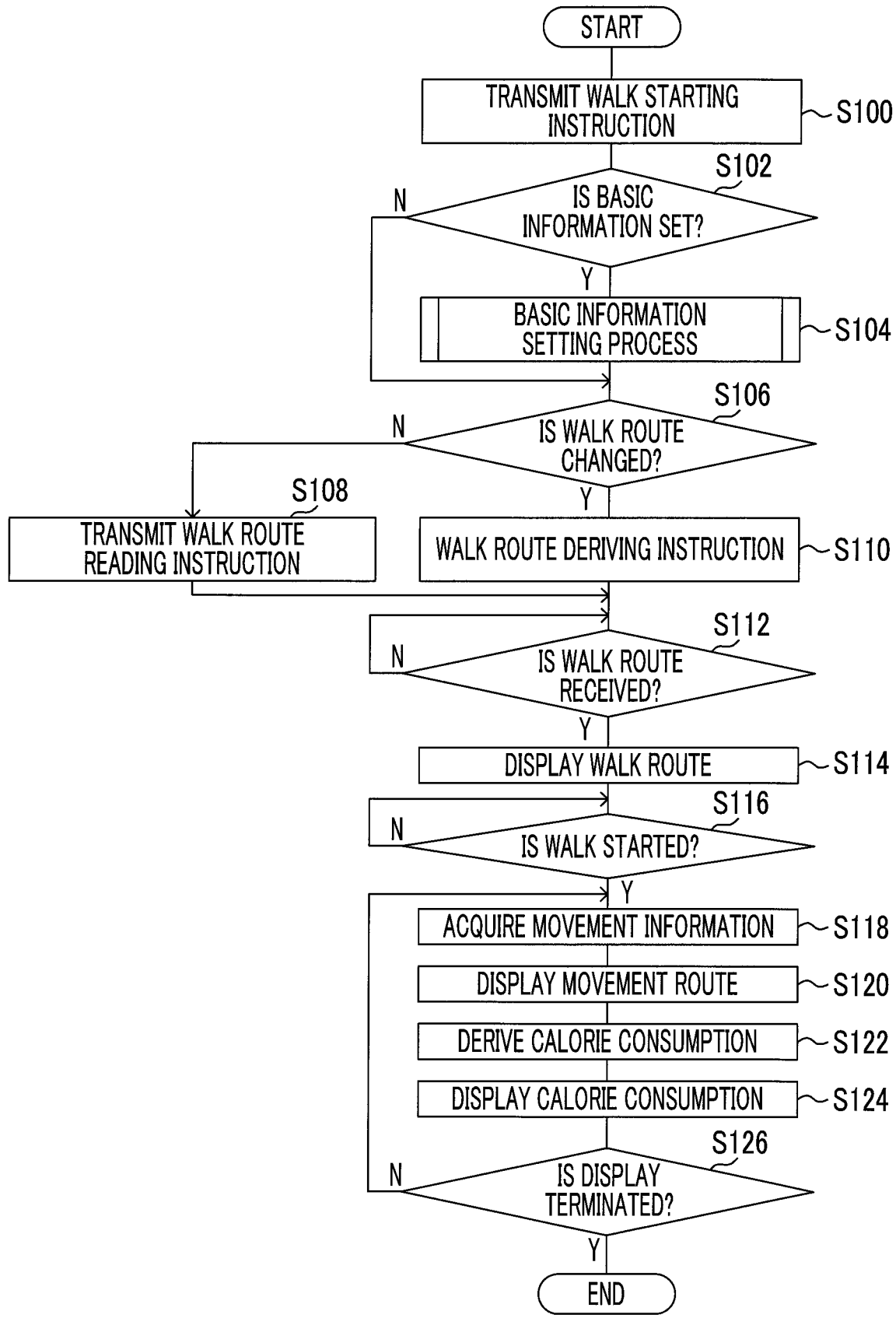
FIG. 9 is a flowchart showing an example of a walk process executed by the owner terminal according to the embodiment.

Next, an operation of the walk support system 1 of this embodiment will be described. First, an operation of the owner terminal 14 will be described with reference to FIG. 9. In this embodiment, the CPU 40 of the owner terminal 14 executes the walk processing program 43A, so that the walk process shown in FIG. 9 is executed. For example, in the walk process of this embodiment shown in FIG. 9, a process of setting the basic information 36, a process of displaying the walk route, and a process of displaying the position and calorie consumption of the owner U (pet P) during a walk.

As an example, in the owner terminal 14 of this embodiment, in a case where the owner U instructs execution of the walk processing program 43A registered as an application program by the input unit 46, a medical condition information acquiring process shown in FIG. 9 is executed.

In step S100 of FIG. 9, the information setting unit 62 transmits a walk start instruction to the walk route deriving device 10 through the network N. The walk start instruction of this embodiment includes a pet ID for identifying a pet P that starts a walk.

In the next step S102, the information setting unit 62 determines whether or not the owner U sets the basic information 36. For example, in this embodiment, a selection screen (not shown) for the owner U to select whether or not to set the basic information 36 is displayed on the display unit 44. The owner U selects whether or not to set the basic information 36 by the input unit 46 in accordance with the selection screen displayed on the display unit 44.

In a case where the owner U does not set the basic information 36, the determination in step S106 is negative, and the procedure proceeds to step S106. On the other hand, in a case where the owner U sets the basic information 36, the determination in step S108 is affirmative, and the procedure proceeds to step S104.

Figure 10:
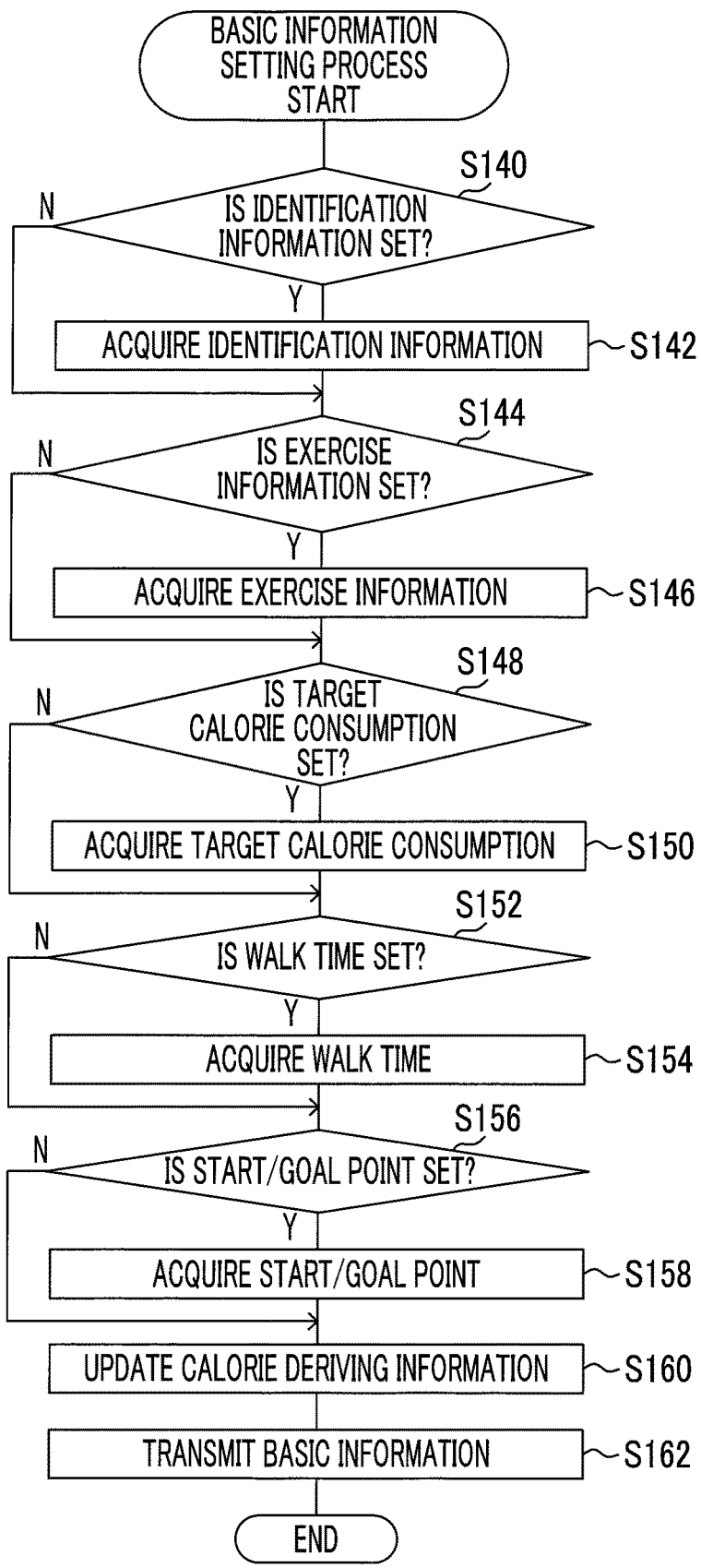
FIG. 10 is a flowchart showing an example of a basic information setting process executed in the walk process shown in FIG. 9.

In step S104, the information setting unit 62 executes a basic information setting process of which an example is shown in FIG. 10.

In step S140 of FIG. 10, the information setting unit 62 determines whether or not to set the above-described identification information in the basic information 36. As an example, in this embodiment, in a case where the owner U selects whether or not to set identification information and the setting is performed, a setting screen (not shown) for inputting a setting value is displayed on the display unit 44. The owner U selects whether or not to set the identification information by the input unit 46 in accordance with the setting screen displayed on the display unit 44.

In a case where the owner U does not set the identification information, the determination in step S140 is negative, and the procedure proceeds to step S144. On the other hand, in a case where the owner U sets the identification information, the determination in step S140 is affirmative, and the procedure proceeds to step S142. In step S142, the information setting unit 62 acquires a setting value of the identification information input by the owner U through the input unit 46 in accordance with the setting screen.

In the next step S144, the information setting unit 62 determines whether or not to set the above-described exercise information in the basic information 36. As an example, in this embodiment, in a case where the owner U selects whether or not to set the exercise information and the setting is performed, a setting screen (not shown) for inputting a setting value is displayed on the display unit 44. The owner U selects whether or not to set the exercise information by the input unit 46 in accordance with the setting screen displayed on the display unit 44.

In a case where the owner U does not set the exercise information, the determination of step S144 is negative, and the procedure proceeds to step S148. On the other hand, in a case where the owner U sets the exercise information, the determination in step S144 is affirmative, and the procedure proceeds to step S146. In step S146, the information setting unit 62 acquires the setting value of the exercise information input by the owner U through the input unit 46 in accordance with the setting screen.

In the next step S148, the information setting unit 62 determines whether or not to set the above-described target calorie consumption in the basic information 36. As an example, in this embodiment, in a case where the owner U selects whether or not to set the target calorie consumption and the setting is performed, a setting screen (not shown) for inputting a setting value is displayed on the display unit 44. The owner U selects whether or not to set the target calorie consumption by the input unit 46 in accordance with the setting screen displayed on the display unit 44.

In a case where the owner U does not set the target calorie consumption, the determination of step S148 is negative, and the procedure proceeds to step S152. On the other hand, in a case where the owner U sets the target calorie consumption, the determination in step S148 is affirmative, and the procedure proceeds to step S150. In step S150, the information setting unit 62 acquires the setting value of the target calorie consumption input by the owner U through the input unit 46 in accordance with the setting screen.

In the next step S152, the information setting unit 62 determines whether or not to set the above-described walk time information in the basic information 36. As an example, in this embodiment, in a case where the owner U selects whether or not to set the walk time and the setting is performed, a setting screen (not shown) for inputting a setting value is displayed on the display unit 44. The owner U selects whether or not to set the walk time by the input unit 46 in accordance with the setting screen displayed on the display unit 44.

In a case where the owner U does not set the walk time, the determination of step S152 is negative, and the procedure proceeds to step S156. On the other hand, in a case where the owner U sets the walk time, the determination in step S152 is affirmative, and the procedure proceeds to step S154. In step S154, the information setting unit 62 acquires the setting value of the walk time input by the owner U through the input unit 46 in accordance with the setting screen.

In the next step S156, the information setting unit 62 determines whether or not to set the above-described start point and goal point in the basic information 36. For example, in this embodiment, in a case where the owner U selects whether or not to set the start point and the goal point and the setting is performed, a setting screen (not shown) for inputting a setting value is displayed on the display unit 44.

The owner U selects whether or not to set at least one of the start point or the goal point through the input unit 46 in accordance with the setting screen displayed on the display unit 44.

In a case where the owner U does not set any one of the start point and the goal point, the determination in step S156 is negative, and the procedure proceeds to step S160. On the other hand, in a case where the owner U sets at least one of the start point or the goal point, the determination in step S156 is affirmative, and the procedure proceeds to step S158. In step S158, the information setting unit 62 acquires the setting value of at least one of the start point or the goal point input by the owner U through the input unit 46 in accordance with the setting screen.

In the next step S160, the information setting unit 62 updates the calorie deriving information 43C stored in the storage unit 42. As an example, the information setting unit 62 of this embodiment updates the calorie deriving information 43C in a case where the weight of the pet P is acquired by the process of step S146. In a case where the weight of the pet P is not acquired through the process of step S146, the process of this step may not be performed.

In the next step S162, the information setting unit 62 transmits the basic information 36 acquired by the above-described respective processes to the walk route deriving device 10 through the network N, and terminates the basic information setting process, and then, the procedure proceeds to step S106 of the walk process shown in FIG. 9.

In step S106, the information setting unit 62 determines whether or not to change a current walk route to be performed from now on from a walk route in a previous (nearest) walk with the pet P. As an example, in this embodiment, a selection screen (not shown) for selecting whether or not to change the walk route by the owner U is displayed on the display unit 44. The owner U selects whether or not to change the walk route by the input unit 46 in accordance with the selection screen displayed on the display unit 44.

In a case where the owner U does not change the walk route, in other words, in a case where the owner U takes a walk along the previous walk route, the determination in step S106 is negative, and the procedure proceeds to step S108. In step S108, the information setting unit 62 transmits a walk route reading instruction to the walk route deriving device 10 through the network N, and then, the procedure proceeds to step S112. On the other hand, in a case where the owner U changes the walk route, the determination in step S106 is affirmative, and the procedure proceeds to step S110. In step S110, the information setting unit 62 transmits the walk route deriving instruction to the walk route deriving device 10 through the network N, and then, the procedure proceeds to step S112.

Figure 11:
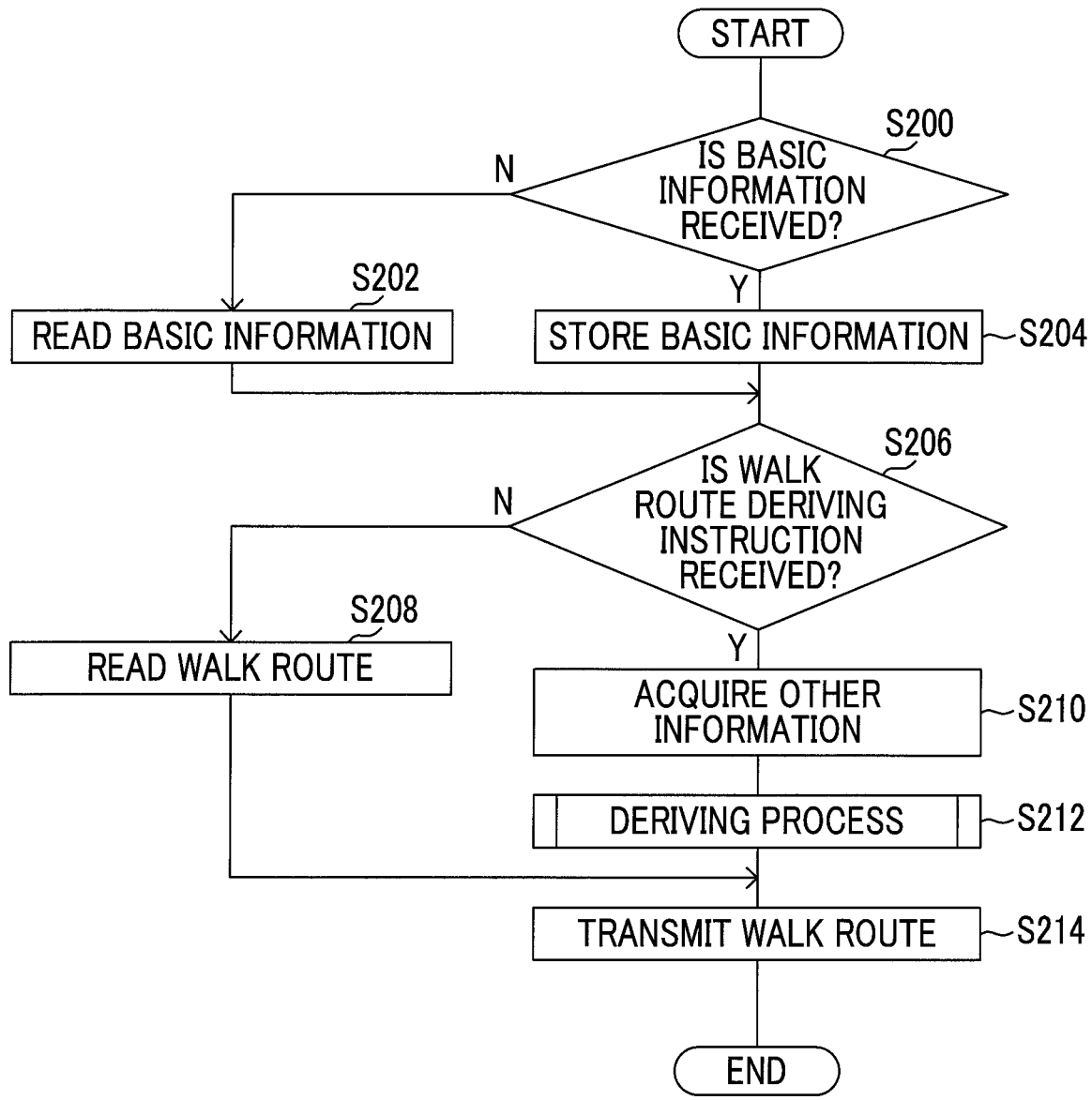
FIG. 11 is a flowchart showing an example of a walk route deriving process executed by the walk route deriving device according to the embodiment.

In the walk route deriving device 10 of the walk support system 1 of this embodiment, in a case where a walk start instruction is received from the owner terminal 14, the walk route deriving process of which an example is shown in FIG. 11 is executed. Here, an operation of deriving a walk route in the walk route deriving device 10 will be described with reference to FIG. 11. In this embodiment, the CPU 20 of the walk route deriving device 10 executes the walk route deriving program 23A, so that the walk route deriving process shown in FIG. 11 is executed. As an example, in the walk route deriving device 10 of this embodiment, as described above, the walk route deriving process shown in FIG. 11 is executed in a case where the walk start instruction is received from the owner terminal 14.

In step S200 of FIG. 11, the acquiring unit 54 determines whether or not the basic information 36 has been received from the owner terminal 14. Specifically, the acquiring unit 54 determines whether or not the basic information 36 transmitted by the owner terminal 14 has been received in step S162 of the above-described basic information setting process (see FIG. 10). In a case where the basic information 36 is not received from the owner terminal 14 even in a case where a predetermined period has elapsed after receiving the walk start instruction, the determination in step S200 is negative, and the procedure proceeds to step S202. In step S202, the deriving unit 50 reads out the basic information 36 associated with a pet ID (hereinafter, referred to as a "pet ID of a pet P taking a walk") included in the received walk start instruction with reference to the basic information 36 stored in the information storage unit 12, and then, the procedure proceeds to step S206.

On the other hand, in a case where the basic information 36 is received from the owner terminal 14, the determination in step S200 is affirmative, and the procedure proceeds to step S204. In step S204, the acquiring unit 54 and the receiving unit 52 store the received basic information 36 as the basic information 36 of the information storage unit 12 in association with the pet ID of the pet P taking a walk. Specifically, the receiving unit 52 receives the walk time in the basic information 36, and stores the received walk time as the basic information 36 of the information storage unit 12 in association with the pet ID of the pet P taking a walk. Further, the acquiring unit 54 acquires information other than the walk time in the basic information 36, and stores the acquired information as the basic information 36 of the information storage unit 12 in association with the pet ID of the pet P taking a walk. In addition, in a case where the basic information 36 associated with the pet ID of the pet P already taking a walk is stored in the information storage unit 12, the basic information 36 stored in the information storage unit 12 is updated to the received basic information 36.

In step S206, the deriving unit 50 determines whether or not to receive a walk route deriving instruction from the owner terminal 14. As described above, in step S108 of the walk process (see FIG. 9) in the owner terminal 14, in a case where the walk route reading instruction transmitted by the owner terminal 14 is received by the walk route deriving device 10, the determination in step S206 is negative, and the procedure proceeds to step S208.

In step S208, the deriving unit 50 reads out information indicating a walk route corresponding to the pet ID of the pet P taking a walk from the walk route DB 38 of the information storage unit 12, and then, the procedure proceeds to step S214.

On the other hand, as described above, in step S110 of the walk process (see FIG. 9) in the owner terminal 14, in a case where the walk route deriving instruction transmitted by the owner terminal 14 is received by the walk route deriving device 10, the determination in step S206 is affirmative, and the procedure proceeds to step S210.

In step S210, the deriving unit 50 acquires other information necessary for derivation of the walk route. Specifically, the deriving unit 50 acquires the position information 37 from the information storage unit 12, and also, acquires the environment information 39. In this embodiment, the environment information 39 is information relating to an environment in which the pet P walks, and includes parameters that represent an environment around the walk route that affects the pet P's walk. The environment information 39 includes information on the day's weather, temperature, humidity, and road information (traffic volume, presence or absence of construction, or the like), and information relating to nearby stores and the like, but is not particularly limited thereto.

Figure 12:
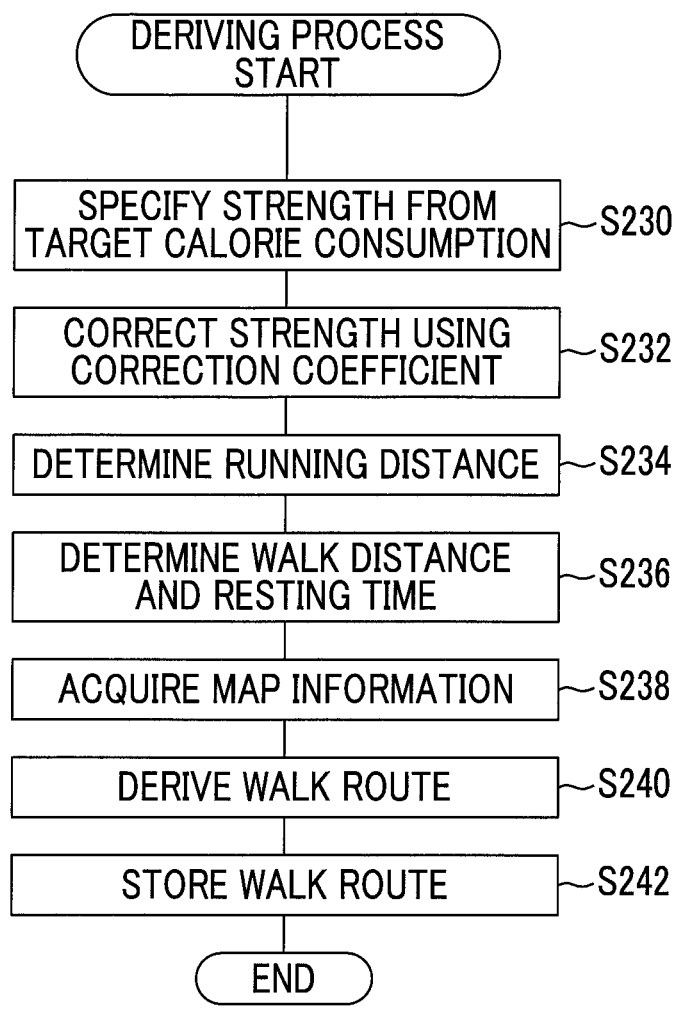
FIG. 12 is a flowchart showing an example of a deriving process executed in the walk route deriving process shown in FIG. 11.

In the next step S212, the deriving unit 50 executes the deriving process of which an example is shown in FIG. 12. In step S230 of FIG. 12, the deriving unit 50 specifies a strength from the target calorie consumption included in the basic information 36. Specifically, the deriving unit 50 in the information storage unit 12 specifies a strength value corresponding to acquired target calorie consumption with reference to the target calorie consumption/strength correspondence information 32.

In the next step S232, the deriving unit 50 corrects the strength specified in the process of step S230 with a correction coefficient. Specifically, the deriving unit 50 acquires a correction coefficient corresponding to each piece of exercise information with reference to corresponding correction coefficient information from the correction coefficient information group 34 for each item such as a dog breed and age in exercise information included in the acquired basic information 36, and sequentially corrects the strength.

For example, a case where the pet P is "Noritama" shown in the basic information 36 shown in FIG. 6 will be specifically described. As shown in the basic information 36, 200 kcal is set in "Noritama" as target calorie consumption. Accordingly, in step S230, the deriving unit 50 acquires "6" that is the strength corresponding to the target calorie consumption of 200 kcal with reference to the target calorie consumption/strength correspondence information 32 (see FIG. 4).

Further, in step S232, since 60 minutes are set as a walk time in "Noritama", the deriving unit 50 acquires "1" which is a correction coefficient corresponding to the walk time of 60 minutes with reference to the walk time correction coefficient information 34A (see FIG. 5A). Further, since Shiba is set as a dog breed of "Noritama", a correction coefficient "1" corresponding to the dog breed of Shiba is acquired with reference to the dog breed correction coefficient information 34B (see FIG. 5B). Further, since "9 years old" is set for "Noritama", a correction coefficient "0.8" corresponding to the age of 9 years old is acquired with reference to the age correction coefficient information 34C (see FIG. 5C). Although correction coefficients corresponding to other exercise information are not shown, according to the correction coefficients, the strength of "Noritama" is corrected according to the following equation (3).

$$\text{Strength "6"} \times \text{correction coefficient "1"} \times \text{correction coefficient "1"} \times \text{correction coefficient "0.8"} = 4.8 \quad (3)$$

The deriving unit 50 of this embodiment corrects the strength using the environment information 39. For example, in a case where the air temperature is higher than a predetermined temperature, generally, it is preferable that the running time is short. In this case, the deriving unit 50 may correct the strength using a correction coefficient corresponding to the temperature included in the environment information 39 while associating the correction coefficient the temperature.

In the next step S234, the deriving unit 50 determines a running distance of the pet P from the strength corrected by the process in step S232. As described above, since the correspondence relationship between the strength and the running distance is stored in the information storage unit 12, the deriving unit 50 determines the running distance on the basis of the stored correspondence relationship.

In the next step S236, the deriving unit 50 determines the walk distance and the resting time of the pet P. As an example, the deriving unit 50 of this embodiment derives the running time from the running distance in accordance with an assumed running speed of the pet P. Generally, since the running speed varies depending on the dog breed or the like, it is preferable to store the assumed running speed in association with each dog breed in the information storage unit 12 or the like, for example. Further, as an example, the deriving unit 50 of this embodiment determines the resting time from the running distance. In this embodiment, since the resting time is set to become longer in consideration of the fatigue of the pet P as the running distance becomes longer, the resting time may be stored in the information storage unit 12 or the like in association with the running distance. The invention is not limited to this embodiment, and the deriving unit 50 may uniquely determine the resting time regardless of the running time, the walk time, or the like, or may determine the resting time in accordance with other exercise information such as an age or the environment information 39 such as weather. That is, the determination method is not particularly limited.

Further, in a case where the running time and the resting time are determined, the deriving unit 50 determines a time obtained by excluding the running time and the resting time from the set walk time as a walk time based on walking (hereinafter, referred to as a "walking time") with reference to the basic information 36 of the information storage unit 12. Further, the deriving unit 50 determines a distance that is recommended for walking of the pet P (hereinafter, referred to as a "walking distance") from the walking time and the assumed walking speed of the pet P. Since the assumed walking speed of the pet P generally varies in accordance with the dog breed, or the like, as in the case of the assumed running speed, for example, it is preferable to store the assumed walking speed in the storage unit 12 or the like in association with each dog breed.

Further, the deriving unit 50 determines a distance obtained by adding the running distance to the walking distance as a walk distance.

In the next step S238, the deriving unit 50 acquires the map information 30 from the information storage unit 12. Further, in the next step S240, the deriving unit 50 derives the walk route on the basis of the acquired map information 30. Specifically, the deriving unit 50 acquires the map information 30 of an area including the start point and the goal point set for the pet P that takes a walk with reference to the basic information 36. As described above, the map information 30 is associated with information necessary for deriving the walk route of the pet P. The deriving unit 50 derives a walk route that satisfies the running distance and the walk distance and passes through the resting place with reference to a place where the pet P can run and a place suitable for the rest of the pet P, which are associated with the map information 30.

In the deriving unit 50 of this embodiment, the position information 37 is also used as described above in deriving a walk route. For example, in a case where the owner U performs a setting for avoiding a position where another pet P lives in or a resting place at a walk route of the other pet P, as the position information 37, the deriving unit 50 derives a walk route that does not include the set position or resting place. In this way, by avoiding the position or the resting place relating to the other pet P, it is possible to derive a preferable walk route for the pet P that is shy or has a habit of barking at other dogs. On the other hand, in a case where the owner U performs a setting for including the position in which the other pet P lives or the resting place at the walk route of the other pet P as the position information 37, the deriving unit 50 derives a walk route including the set position or resting place. In this way, by including the position or the resting place relating to the other pet P, it is possible to derive a preferable walk route for the pet P that likes to play with other dogs or has many friends.

In the next step S242, the deriving unit 50 stores information indicating the walk route derived in step S240 in the walk route DB 38 of the information storage unit 12, and terminates the present deriving process, and then, the procedure proceeds to step S214 of the walk route deriving process shown in FIG. 11. Details of the walk route will be described later.

In step S214, the deriving unit 50 transmits information indicating the walk route derived by the deriving process in the above-described step S212 to the owner terminal 14 through the network N, and then terminates the walk route deriving process.

As described above, the walk route deriving device 10 of this embodiment derives the walk route, but in the walk route derived as described above, there is a case where the pet P cannot yet consume the target calorie. In such a case, for example, by increasing the running speed in accordance with the strength, the amount of exercise of the pet P may be increased to increase the calorie consumption. Further, for example, by changing a running place to a place where the amount of exercise increases, such as an uphill, from a flat place in accordance with the strength, the amount of exercise of the pet P may be increased to increase the calorie consumption.

The owner terminal 14 receives information indicating the walk route transmitted from the walk route deriving device 10 through the network N. Accordingly, the display controller 60 of the owner terminal 14 determines whether or not information indicating a walk route has been received in step S112 of the above-described walk process (see FIG. 9). Until the information indicating the walk route is received, the determination in step S112 is negative. On the other hand, in a case where the information indicating the walk route is received, the determination in step S112 is affirmative, and the procedure proceeds to step S114.

Figure 13:
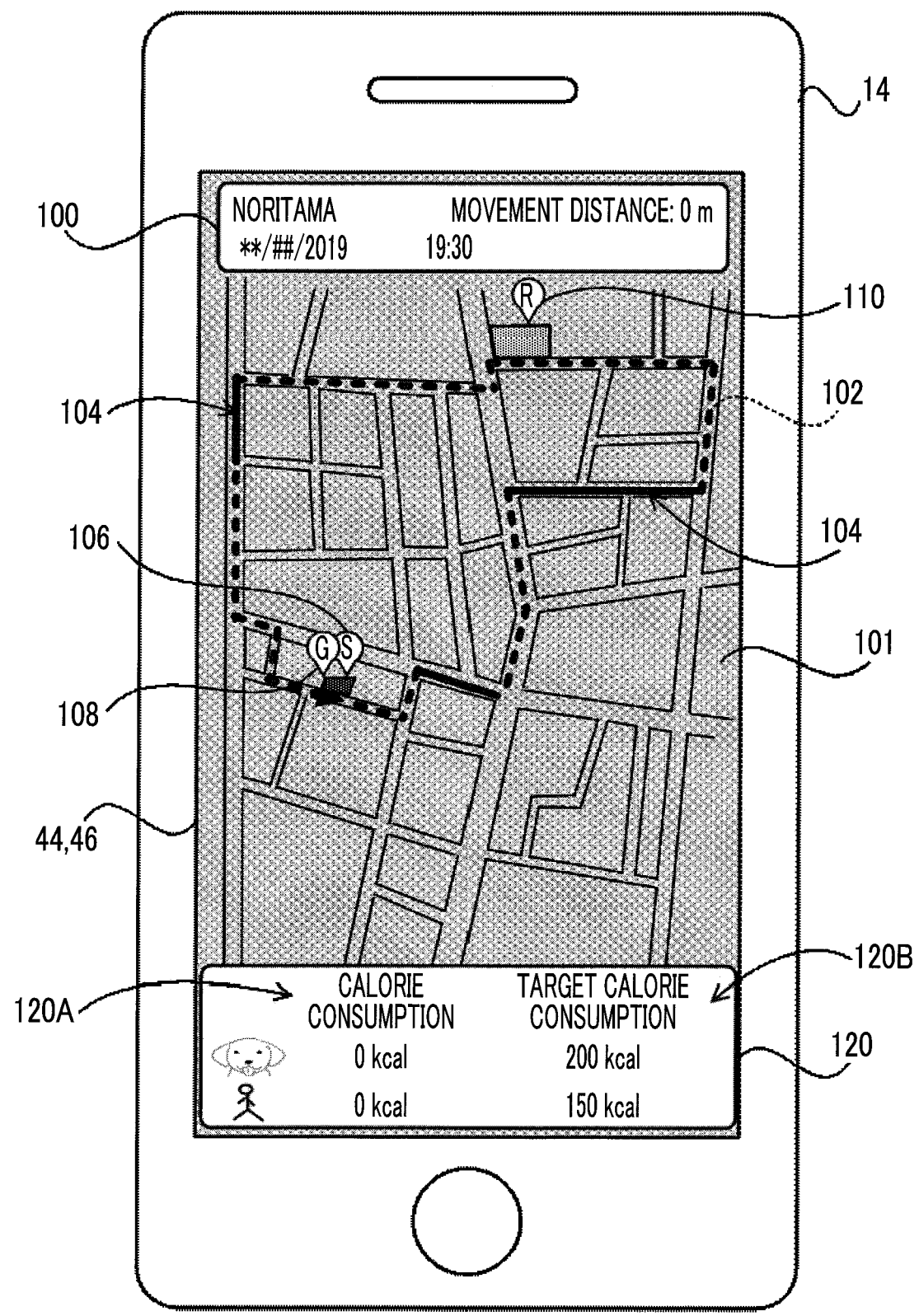
FIG. 13 is a diagram showing an example of a state where a walk route is displayed on a display unit of the owner terminal.

In step S114, the display controller 60 causes the display unit 44 to display a walk route corresponding to the received information indicating the walk route. FIG. 13 shows an example of a walk route 102 displayed on the display unit 44 of the owner terminal 14. FIG. 13 shows an example in a state where a map 101 with the walk route 102 attached is displayed on the display unit 44.

In the example shown in FIG. 13, a running place 104 is indicated by a solid line in a part of the walk route 102 indicated by a broken line. A specific display format of the walk route 102 and the running place 104 is not particularly limited, but it is preferable to use a display format in which the running place 104 is more conspicuous than the walk route 102.

Further, in the example shown in FIG. 13, a mark 106 indicating a start point, a mark 108 indicating a goal point, and a mark 110 indicating a resting place are displayed on the map. In addition, in the example shown in FIG. 13, the display unit 44 of the owner terminal 14 displays, as the basic information 100, information indicating a name of the pet P, current date and time, and a movement distance indicating a walk distance.

In the example shown in FIG. 13, a state where the calorie consumption information 120 is displayed on the display unit 44 is shown, but since the display of the calorie consumption information 120 is performed in a later process, this will be described later.

In the next step S116, the position detecting unit 64 determines whether or not the pet P (owner U) has started taking a walk. As an example, the position detecting unit 64 of this embodiment determines that the pet P has started taking a walk in a case where the position of the owner U has changed by a predetermined distance or more, on the basis of a detection result of the position detecting sensor 47. The determination in step S116 is a negative determination until the pet P starts taking a walk. On the other hand, in a case where the pet P starts taking a walk, the determination in step S116 is affirmative, and the procedure proceeds to step S118.

Figure 14:
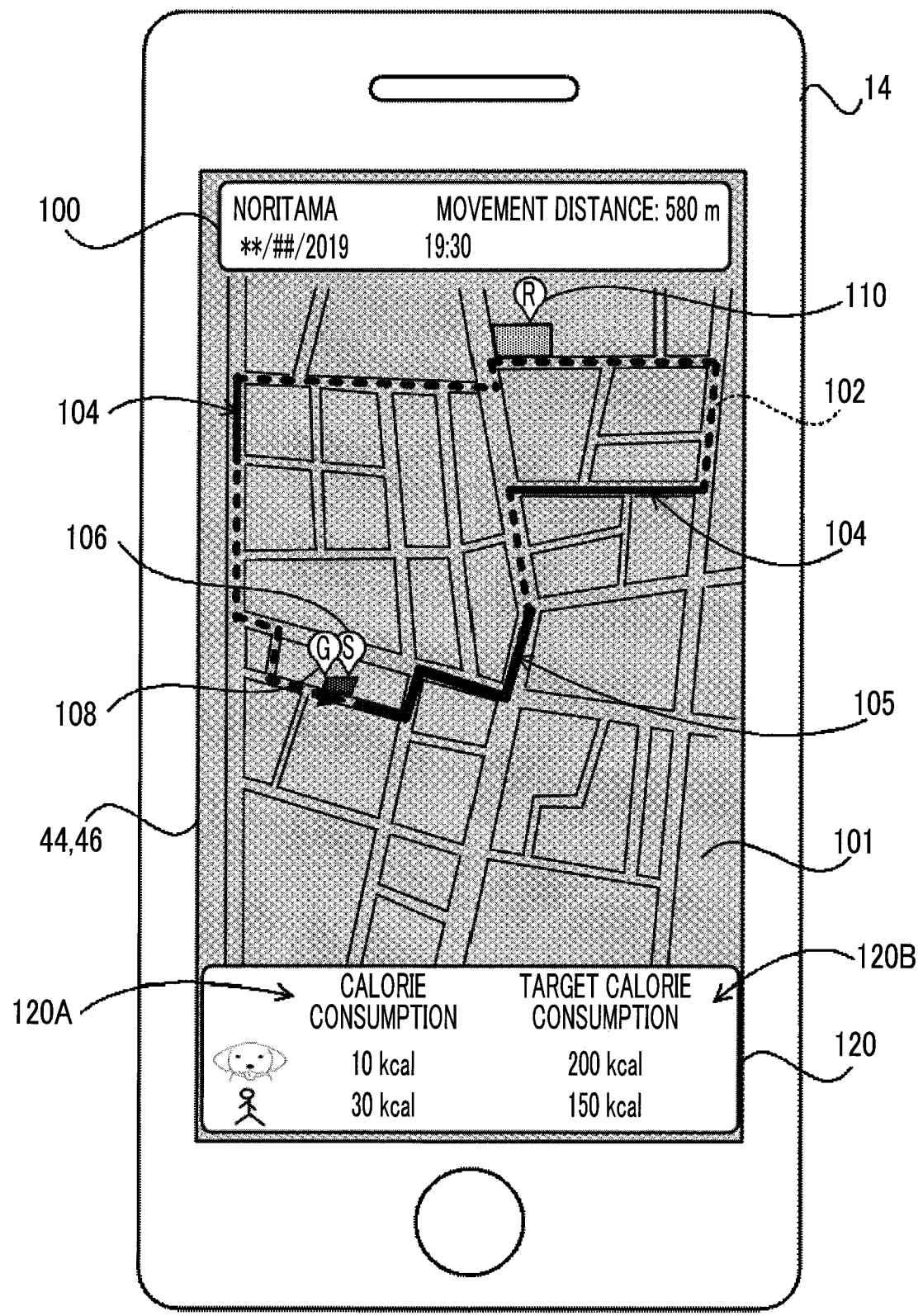
FIG. 14 is a diagram showing an example of a state where a walk route is displayed on the display unit of the owner terminal.

In step S118, the position detecting unit 64 acquires movement information of the pet P, and in the next step S120, the display controller 60 displays a movement route of the pet P (owner U) on the display unit 44 on the basis of the acquired movement information. Specifically, the position detection unit 64 derives a route through which the owner U moves on the basis of the detection result of the position detecting sensor 47, and the display controller 60 displays the movement route on the display unit 44 as a route 105, as in the example shown in FIG. 14.

In the next step S122, the calorie consumption deriving unit 66 derives calorie consumption consumed by each of the pet P and the owner U from the start of the walk. As an example, the calorie consumption deriving unit 66 according to this embodiment derives the calorie consumption of the pet P using information indicating the movement distance received from the pet terminal 16.

As an example, the calorie consumption deriving unit 66 of this embodiment derives energy requirement for running (ERR) as the calorie consumption of the pet P by the following equation (4). In the following equation (4), "d" represents a movement distance (km), and "weight" represents a weight of the pet P.

$$\text{ERR}=(1.77d\times\text{weight}^{-0.4})+(1.25\times\text{weight}^{-0.25}) \qquad (4)$$

Further, as an example, the calorie consumption deriving unit 66 measures a time since the start of the walk as an exercise time, and derives the calorie consumption of the owner U by the following equation (5) using the measured exercise time. Here, "METs" in the following equation (5) is a unit of an exercise strength that represents how many times the amount of energy consumed by exercise is the amount of energy consumed at rest, and "weight" represents a weight of the owner U.

$$\text{METs}\times\text{weight}\times\text{exercise time}\times1.05 \qquad (5)$$

In the next step S124, the display controller 60 causes the display unit 44 of the owner terminal 14 to display the consumption calorie derived by the calorie consumption deriving unit 66. In addition, the display controller 60 of this embodiment causes the display unit 44 to display the target calorie consumption of each of the pet P and the owner U. In the examples shown in FIGS. 13 and 14, the calorie consumption information 120 displayed on the display unit 44 includes calorie consumption 120A and target calorie consumption 120B of each of the pet P and the owner U.

In the next step S126, the display controller 60 determines whether or not to terminate the display of the walk route 102. In the owner terminal 14 of this embodiment, in a case where the display of the walk route 102 is terminated, the display of the map 101 is also terminated. Until the owner U instructs the termination of the display through the input unit 46 of the owner terminal 14, the determination in step S126 is negative, and the procedure returns to step S118, so that the processes of steps S118 to S124 are repeated. On the other hand, in a case where the owner U gives an instruction to terminate the display through the input unit 46, the determination in step S126 is affirmative, and the walk process is terminated.

According to the walk support device 11 obtained by the walk route deriving device 10 and the owner terminal 14 of this embodiment, the walk route 102 including the running place 104 may be displayed on the display unit 44 of the owner terminal 14 on the basis of the basic information 36 of the pet P.

Further, in the walk support system 1 of this embodiment, the owner U can browse a walk route of another pet P different from his/her pet P. An operation in a case where the walk route of another pet P is browsed in the walk route deriving device 10 and the owner terminal 14 will be described.

First, an operation of the owner terminal 14 will be described with reference to FIG. 15. In this embodiment, the CPU 40 of the owner terminal 14 executes the walk route browsing program 43B to execute the walk route browsing process shown in FIG. 15. As an example, in the owner terminal 14 of this embodiment, in a case where the owner U gives an instruction to browse the walk route of another pet P through the input unit 46, the walk route browsing process shown in FIG. 15 is executed.

Figure 15:
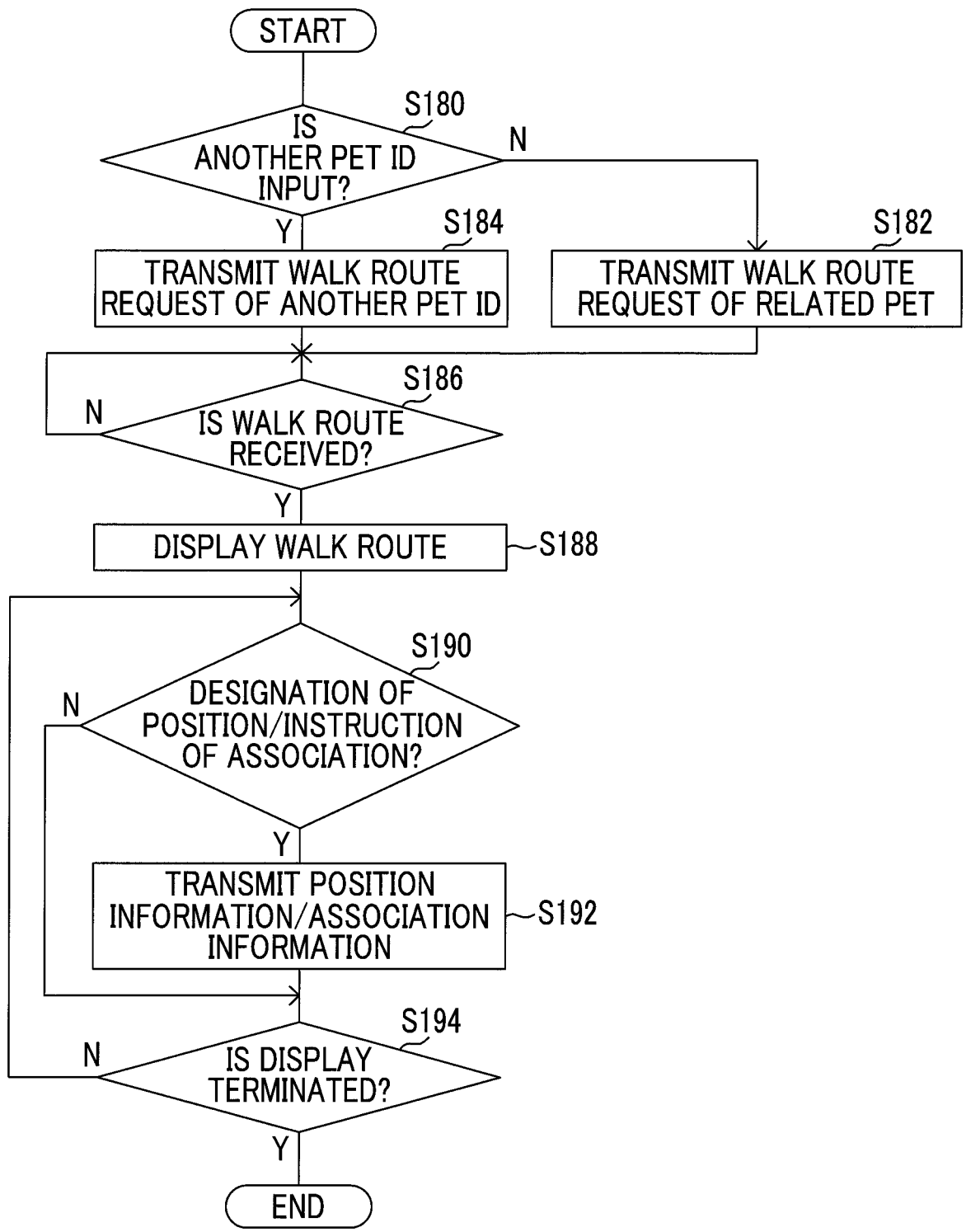
FIG. 15 is a flowchart showing an example of a walk route browsing process executed by the owner terminal according to the embodiment.

In step S180 of FIG. 15, the display controller 60 determines whether a pet ID of another pet P has been input. In the walk support system 1 of this embodiment, as described above, the walk route of the pet P stored in the walk route DB 38 is associated with identification information (pet ID) of another pet P relating to the present pet (hereinafter referred to as a "related pet") or a related pet P relating to the owner U of the pet P. Accordingly, in a case where the walk route of the related pet P is browsed, the owner U inputs the pet ID of his/her pet P through the input unit 46, and also inputs an instruction to browse the walk route of the related pet P through the input unit 46. On the other hand, the owner U can input the pet ID of another pet through the input unit 46 to browse the walk route of the other pet P corresponding to the input pet ID.

In a case where the pet ID of another pet P has not been input, in other words, in a case where an instruction to browse the pet ID of the pet P of the owner U and the walk route of the related pet P has been input, the determination in step S180 is negative, and the procedure proceeds to step S182.

In step S182, the display controller 60 transmits the pet ID of the pet P and a request for the walk route of the related pet P to the walk route deriving device 10 through the network N, and then, the procedure proceeds to step S186.

On the other hand, in a case where the pet ID of another pet P is input, the determination in step S180 is affirmative, and the procedure proceeds to step S184. In step S184, the display controller 60 transmits the pet ID of the other pet P and a request for the walk route corresponding to the pet ID to the walk route deriving device 10 through the network N, and then, the procedure proceeds to step S186. Through the process of step S182 or step S184, information indicating the walk route is transmitted from the walk route deriving device 10 to the owner terminal 14 through the network N (of which details will be described later).

In the next step S186, the display controller 60 determines whether or not the information indicating the walk route has been received. Until the information indicating the walk route is received, the determination in step S186 is negative.

On the other hand, in a case where the information indicating the walk route is received, the determination in step S186 is affirmative, and the procedure proceeds to step S188.

In step S188, the display controller 60 causes the display unit 44 of the owner terminal 14 to display the walk route corresponding to the received information indicating the walk route. The display unit 44 is in a state where the map 101 in which the walk route 102 is added is displayed in the same manner as the map 101 shown in FIG. 13.

As an example, in the walk support system 1 according to this embodiment, the owner U may set at least one of the position information 37 or association between the pet P and another pet P on the basis of the walk route displayed on the display unit 44. For example, in the walk support system 1, in a case where the owner U designates (clicks) a mark 110 indicating a resting place with reference to the map 101 displayed on the display unit 44, a place indicating the designated position is set as the position information 37. In this way, by setting the place indicating the position designated by the owner U as the position information 37, the deriving unit 50 of the walk route deriving device 10 can derive a walk route that includes the designated place, and contrarily, can derive a walk route that does not include the designated place, as described above. Further, the owner U can associate other pets P whose walk route is displayed on the display unit 44 with his/her pet P by instructing the association by the input unit 46.

In step S190, the display controller 60 determines whether or not the owner U has performed at least one of the designation of the position or the instruction of the association through the input unit 46. In a case where the owner U has not performed either of the designation of the position or the instruction of the association, the determination in step S190 is negative, and the procedure proceeds to step S194. On the other hand, in a case where the owner U has performed at least one of the designation of the position or the association, the determination in step S190 is affirmative, and the procedure proceeds to step S192.

In step S192, the display controller 60 transmits the information indicating the designated position and the association instruction performed by the owner U to the walk route deriving device 10 through the network N. In the next step S194, the display controller 60 determines whether or not to terminate the display of the walk route 102. Until the owner U instructs the termination of the display through the input unit 46 of the owner terminal 14, the determination in step S194 is negative, and the procedure returns to step S190, and then, the processes of steps S190 and S192 are repeated. On the other hand, in a case where the owner U instructs the termination of the display through the input unit 46, the determination in step S194 is affirmative, and the walk route browsing process is terminated.

In this way, in the owner terminal 14 of this embodiment, the owner U can also browse a walk route of the pet P other than his/her pet P. Accordingly, for example, in a case where a walk route of his/her pet P overlaps a walk route of another pet P, the owner U can shift a walk time, or can adjust the walk time.

Next, an operation of the walk route deriving device 10 will be described with reference to FIG. 16. In this embodiment, the CPU 20 of the walk route deriving device 10 executes the walk route providing program 23B to execute the walk route providing process shown in FIG. 16. As an example, in a case where the walk route deriving device 10 of this embodiment receives a request for a walk route transmitted from the owner terminal 14 in step S182 or step S184 of the walk route browsing process (see FIG. 15), the walk route providing process shown in FIG. 16 is executed.

In step S280 of FIG. 16, the deriving unit 50 determines whether or not the received request is a request for a pet ID of the pet P and a walk route of a related pet P. In a case where the received request is the request for the pet ID of the pet P and the walk route of the related pet P, the determination in step S280 is affirmative, and the procedure proceeds to step S282.

In step S282, the deriving unit 50 acquires information indicating the walk route of the related pet P, and then, the procedure proceeds to step S286. Specifically, the deriving unit 50 specifies a pet ID of the related pet P associated with the received pet ID of the pet P with reference to the walk route DB 38. Further, the deriving unit 50 acquires the information indicating the walk route associated with the specified pet ID with reference to the walk route DB 38.

On the other hand, in a case where the received request is not the request for the pet ID of the pet P and the walk route of the related pet P, in other words, in a case where the received request is a request for a pet ID of another pet P and a walk route corresponding to the pet ID, the determination in step S280 is negative, and the procedure proceeds to step S284. In step S284, the deriving unit 50 acquires information indicating the walk route of another pet P. Specifically, the deriving unit 50 acquires the information indicating the walk route associated with the received pet ID of the pet P with reference to the walk route DB 38.

In the next step S286, the deriving unit 50 transmits the acquired information indicating the walk route to the owner terminal 14 through the network N. In the next step S290, the deriving unit 50 determines whether or not the information indicating the designated position and the association instruction performed by the owner U, which are transmitted from the owner terminal 14 in step S192 of the walk route browsing process (see FIG. 15), has been received. Even though a predetermined period elapses after the process of step S286 is performed, in a case where neither the information indicating the designated position nor the association instruction has been received, the determination in step S290 is negative, and the walk route providing process is terminated.

On the other hand, in a case where at least one of the information indicating the designated position or the association instruction has been received, the determination in step S290 is affirmative, and the procedure proceeds to step S292. In step S292, the deriving unit 50 stores the position information and the association information in the information storage unit 12, and then, the walk route providing process is terminated. Specifically, in a case where the information indicating the designated position has been received, the deriving unit 50 sets the received information in the position information 37 as position information. Further, in a case where the association instruction has been received, the deriving unit 50 stores the received pet ID in association with a pet ID of a corresponding pet P in the walk route DB 38.

As described above, in the walk route deriving device 10 of this embodiment, since setting of the position information 37 or association of the pet P is performed, in deriving the walk route of the pet P, it is possible to use information such as the position information 37, and to derive a more appropriate walk route.

As described above, the walk support device 11 according to this embodiment is configured so that the walk route deriving device 10 comprises the acquiring unit 54 that acquires exercise information for specifying the amount of exercise necessary for the pet P, and the deriving unit 50 that derives a walk route of the pet P including a running place of the pet P on the basis of the exercise information.

There is a case where a walk time of the pet P may be determined by the owner U, for example, regardless of the state or convenience of the pet P. In such a case, there is a case where the amount of exercise does not satisfy the amount of exercise necessary for the pet P just by taking a walk only by walking.

In the walk route deriving device 10 of this embodiment, as described above, it is possible to increase the amount of exercise of the pet P within a predetermined walk time by including a running place of the pet P in a walk route. Accordingly, according to the walk route deriving device 10 of this embodiment, it is possible to efficiently walk the pet P in a short time.

In this embodiment, a configuration in which the owner terminal 14 displays the walk route 102 on the display unit 44 has been described, but the display method of the walk route 102 and the running place 104 is not limited to this embodiment. For example, instead of performing a visual display on the display unit 44, or in addition to performing the visual display on the display unit 44, an audible display may be performed by sound through the output unit 45. For example, as in the case of a vehicle navigation system, a method for instructing which direction a walk is to be taken in by sound, for example, and giving a running instruction by sound in reaching a running place may be used. Further, for example, a method for outputting rhythm sound through the output unit 45 and increasing the pace (rhythm) of the rhythm sound during running compared with walking may be used.

Further, for example, a configuration in which the owner terminal 14 compares an actual running route of the pet P detected by the position detecting unit 64 with a walk route derived by the deriving unit 50 of the walk route deriving device 10 and provides the comparison result to the owner U or stores the comparison result may be used. Further, for example, a configuration in which the owner terminal 14 determines whether or not the pet P has run a running place included in the walk route derived by the deriving unit 50 and provides the determination result to the owner U or stores the determination result may be used. Whether or not the pet P (owner U) is running may be derived from a movement distance detected by the position detecting unit 64 and a movement time required for the movement distance.

Further, in this embodiment, a configuration in which calorie consumption of the pet P is derived from a movement distance of the pet P received from the pet terminal 16 has been described, but a configuration in which the calorie consumption of the pet P is derived by a movement distance detected by the position detecting unit 64 of the owner terminal 14 may be used. In this case, since the movement distance of the pet P and the movement distance of the owner U do not completely match each other, there is an effect that it is not necessary to use the pet terminal 16 although the accuracy is slightly lowered. Further, since it is not necessary to use the pet terminal 16, it is possible to eliminate troublesomeness of the pet P caused by wearing the pet terminal 16.

Further, in this embodiment, as described above, a configuration in which the walk route deriving device 10 derives a walk route including a running place, but in the case of a pet P for which running is not preferable, a configuration in which a walk route that does not include the running place is derived may be used. For example, in the case of a pet P of a relatively old age or a young pet P with little experience of a walk, a configuration in which the walk route deriving device 10 sets a value of the strength to "0" so that a walk route that does not include a running place is derived may be used.

Further, in this embodiment, a configuration in which it is possible to browse a walk route of another pet P has been described, but a configuration in which it is possible to set whether or not to allow other persons to browse a walk route of the own pet P in accordance with a request from the owner U may be used. In this case, for example, in a case where the walk route deriving device 10 stores the walk route set by the owner U in the walk route DB 38 in association with the pet ID, the walk route deriving device 10 may store information indicating whether or not to allow other persons to browse the walk route of the pet P, set by the owner U, in association therewith. Further, a configuration in which, in a case where the walk route deriving device 10 that receives a request for a walk route from the owner terminal 14 performs the walk route providing process, in a case where the browsing of the walk route is not allowed with respect to the pet P for which the walk route is requested, the walk route is not provided, may be used.

Further, the functions of the owner terminal 14 are not limited to this embodiment. For example, the owner terminal 14 may have a function of creating a group among a plurality of owners U. In addition, the owner terminal 14 may have a function of allowing communication between the grouped owners U through the owner terminal 14. By having such a function, the owners U can communicate with each other, and thus, it is possible to adjust a time at which each pet P takes a walk, or to make a meeting at a desired resting place. In this case, for example, a configuration in which the walk route deriving device 10 detects a resting place that becomes a meeting place, a time to take a walk, and the like from the content of communication (conversation) between the owners U through the owner terminal 14 and reflects the detection result in deriving the walk route of the pet P of each owner U may be used. In addition, for example, a configuration in which each of the plurality of owners U who communicates with each other sets a resting place that becomes a meeting place, a time to take a walk, and the like through the owner terminal 14 and the walk route deriving device 10 reflects the setting result in deriving the walk route of the pet P of each owner U may be used.

Further, in this embodiment, a configuration in which the walk route deriving device 10 derives a walk route in which completion of a walk is possible within a set walk time has been described, but the invention is not limited to this embodiment. For example, in a case where a diet mode that prioritizes increase of the amount of exercise is provided the walk route deriving device 10 and the diet mode is designated, the deriving unit 50 may derive a walk route where actual calorie consumption of the pet P is equal to or greater than target calorie consumption regardless of a set walk time.

In addition, in this embodiment, a configuration in which the walk support device 11 is configured by the walk route deriving device 10 and the owner terminal 14, respectively has been described, the walk support device 11 is not limited to this embodiment. For example, a configuration in which the walk route deriving device 10 or the owner terminal 14 has all the functions of the walk support device 11 may be used.

Further, in this embodiment, a configuration in which the walk support system 1 supports the walk of the pet P has been described, but a configuration in which the walk support system 1 (walk support device 11) supports a human walk other than the pet P, for example, may be used. In a case where the pet P is a human being, similarly, it is possible to take a walk efficiently in a short time.

Further, in the above embodiment, various processors other than the CPU may execute various processes executed as the CPU executes software (programs). In this case, as the processors, a programmable logic device (PLD) of which a circuit configuration is changeable after manufacturing, such as a field-programmable gate array (FPGA), a dedicated electric circuit that is a processor having a circuit configuration that is exclusively designed to execute a specific process, such as an application specific integrated circuit (ASIC), and the like are exemplified. Further, the various processes may be executed by one of the various processors, or may be executed by combination of two or more processors of the same type or different types (for example, combination of a plurality of FPGAs or combination of a CPU and an FPGA). In addition, a hardware structure of the various processors is, more specifically, an electric circuit in which circuit elements such as semiconductor elements are combined.

Further, in the above-described embodiment, a configuration in which the walk route deriving program 23A and the walk route providing program 23B are stored (installed) in the storage unit 22 in advance and the walk processing program 43A and the walk route browsing program 43B are stored in the storage unit 42 in advance has been described, but the invention is not limited thereto. Each of the walk route deriving program 23A, the walk route providing program 23B, the walk processing program 43A, and the walk route browsing program 43B may be provided in a state of being recorded in a recording medium such as a compact disk read only memory (CD-ROM), a digital versatile disk read only memory (DVD-ROM), or a universal serial bus (USB) memory. Further, each of the walk route deriving program 23A, the walk route providing program 23B, the walk processing program 43A, and the walk route browsing program 43B may be downloaded from an external device through a network.

According to a second aspect of the present disclosure, in the walk support device according to the first aspect, a correspondence relationship between a target calorie consumption to be consumed by the pet by a walk and a strength relating to running of the pet, and the processor derives the walk route on the basis of the strength based on the target calorie consumption and the exercise information.

According to a third aspect of the present disclosure, in the walk support device according to the second aspect, in the correspondence relationship, the strength is associated so that at least one of a distance where the pet is recommended to run or a time when the pet is recommended to run becomes longer as the target calorie consumption becomes higher.

According to a fourth aspect of the present disclosure, in the walk support device according to the second or third aspect, the processor derives the walk route on the basis of the strength corrected in accordance with a walk time necessary for the pet to walk and the exercise information.

According to a fifth aspect of the present disclosure, in the walk support device according to the fourth aspect, the processor receives designation of the walk time.

According to a sixth aspect of the present disclosure, in the walk support device according to any one of the first to fifth aspects, the exercise information includes information relating to at least one of a dog breed, an age, a gender, a weight, castration, or disease of the pet.

According to a seventh aspect of the present disclosure, in the walk support device according to any one of the first to sixth aspects, the processor derives the walk route further on the basis of environment information relating to an environment where a walk is performed.

According to an eighth aspect of the present disclosure, in the walk support device according to any one of the first to seventh aspects, the processor derives the walk route further on the basis of position information relating to a position of another pet.

According to a ninth aspect of the present disclosure, in the walk support device according to any one of the first to eighth aspects, the processor derives the walk route including a place where the pet is recommended to rest, and displays the walk route on a display unit in a state where the place where the pet is recommended to run and the place where the pet is recommended to rest can be identified.

According to a tenth aspect of the present disclosure, the walk support device according to any one of the first to ninth aspects further comprises a second processor that controls a display unit to display information indicating calorie consumption of the pet during walk of the pet on the walk route.

According to an eleventh aspect of the present disclosure, in the walk support device according to the tenth aspect, the second processor controls the display unit to display information indicating calorie consumption of a person who takes a walk with the pet.

According to a twelfth aspect of the present disclosure, in the walk support device according to the eleventh aspect, the second processor controls the display unit to display information corresponding to a target calorie consumption to be consumed by the person and a calorie consumption consumed by the walk.

According to a thirteenth aspect of the present disclosure, in the walk support device according to any one of the first to twelfth aspect, the processor acquires the exercise information of each of a plurality of the pets, the processor derives the walk route with respect to each of the plurality of pets, and an owner of a certain pet among the plurality of pets is able to browse the walk route relating to another pet.

According to a fourteenth aspect of the present disclosure, the walk support device according to any one of the first to thirteenth aspect further includes a memory that stores the walk route in a state of being associated with at least one of another pet relating to the pet that takes a walk on the walk route or another owner relating to an owner of the pet that takes a walk on the walk route.

Furthermore, an information processing apparatus according to the present disclosure comprises a memory that stores a command for execution of a computer and a processor configured to execute the stored command, in which the processor acquires exercise information for specifying the amount of exercise necessary for a pet and derives a walk route of the pet including a place where the pet is recommended to run on the basis of the exercise information.

According to the present disclosure, it is possible to efficiently walk a pet in a short time.

What is claimed is:

1. A walk support device comprising a processor that is configured to:
  acquire exercise information for specifying an amount of exercise necessary for a pet; and
  derives a walk route of the pet including a place where the pet is recommended to run on the basis of the exercise information, wherein a correspondence relationship is set in advance between a target calorie consumption to be consumed by the pet by a walk and a strength, which indicates a degree of running by the pet compared to walking by the pet over the walk route, and
  the processor corrects the strength based on the exercise information, and derives the walk route on the basis of the corrected strength corresponding to the target calorie consumption and the exercise information.

2. The walk support device according to claim 1,
wherein in the correspondence relationship, the strength is associated so that at least one of a distance where the pet is recommended to run or a time when the pet is recommended to run becomes longer as the target calorie consumption becomes higher.

3. The walk support device according to claim 1,
wherein the processor derives the walk route on the basis of the strength corrected in accordance with a walk time necessary for the pet to walk and the exercise information.

4. The walk support device according to claim 3,
wherein the processor receives designation of the walk time.

5. The walk support device according to claim 1,
wherein the exercise information includes information relating to at least one of a dog breed, an age, a gender, a weight, castration, or disease of the pet.

6. The walk support device according to claim 1,
wherein the processor derives the walk route further on the basis of environment information relating to an environment where a walk is performed.

7. The walk support device according to claim 1,
wherein the processor derives the walk route further on the basis of position information relating to a position of another pet.

8. The walk support device according to claim 1,
wherein the processor derives the walk route including a place where the pet is recommended to rest, and causes a display unit to display the walk route in a state where the place where the pet is recommended to run and the place where the pet is recommended to rest can be identified.

9. The walk support device according to claim 1, further comprising:
  a second processor that controls a display unit to display information indicating calorie consumption of the pet during walk of the pet on the walk route.

10. The walk support device according to claim 9,
wherein the second processor controls the display unit to display information indicating calorie consumption of a person who takes a walk with the pet.

11. The walk support device according to claim 10,
wherein the second processor further controls the display unit to display information corresponding to a target calorie consumption to be consumed by the person and a calorie consumption consumed by the walk.

12. The walk support device according to claim 1,
wherein the processor acquires the exercise information of each of a plurality of the pets, the deriving unit derives the walk route with respect to each of the plurality of pets, and an owner of a certain pet among the plurality of pets is able to browse the walk route relating to another pet.

13. The walk support device according to claim 1, further comprising:
  a memory that stores the walk route in a state of being associated with at least one of another pet relating to the pet that takes a walk on the walk route or another owner relating to an owner of the pet that takes a walk on the walk route.

14. A walk support method comprising:
by a processor,
    acquiring exercise information for specifying an amount of exercise necessary for a pet; and
    deriving a walk route of the pet including a place where the pet is recommended to run, wherein
a correspondence relationship is set in advance between a target calorie consumption to be consumed by the pet by a walk and a strength, which indicates a degree of running by the pet compared to walking by the pet over the walk route, and
the processor corrects the strength based on the exercise information, and derives the walk route on the basis of the corrected strength corresponding to the target calorie consumption and the exercise information.

15. A non-transitory computer-readable storage medium storing a walk support program for causing a computer:
    acquire exercise information for specifying an amount of exercise necessary for a pet; and
    derive a walk route of the pet including a place where the pet is recommended to run on the basis of the exercise information, wherein
a correspondence relationship is set in advance between a target calorie consumption to be consumed by the pet by a walk and a strength, which indicates a degree of running by the pet compared to walking by the pet over the walk route, and
a processor of the computer corrects the strength based on the exercise information, and derives the walk route on the basis of the corrected strength corresponding to the target calorie consumption and the exercise information.

\* \* \* \* \*